(12) United States Patent
Wozencroft

(10) Patent No.: US 11,058,555 B2
(45) Date of Patent: Jul. 13, 2021

(54) HOLDER FOR AN ACETABULAR CUP IMPLANT

(71) Applicant: EMBODY ORTHOPAEDIC LTD, Lodon (GB)

(72) Inventor: Robert Michael Wozencroft, Central London (GB)

(73) Assignee: Embody Orthopaedic Limited, London (GB)

( * ) Notice: Subject to any disclaimer, the term of this patent is extended or adjusted under 35 U.S.C. 154(b) by 197 days.

(21) Appl. No.: 16/314,195

(22) PCT Filed: Jul. 12, 2017

(86) PCT No.: PCT/GB2017/052039
§ 371 (c)(1),
(2) Date: Dec. 28, 2018

(87) PCT Pub. No.: WO2018/011568
PCT Pub. Date: Jan. 18, 2018

(65) Prior Publication Data
US 2019/0201215 A1 Jul. 4, 2019

(30) Foreign Application Priority Data
Jul. 12, 2016 (GB) ..................... 1612056

(51) Int. Cl.
*A61F 2/46* (2006.01)
*A61F 2/34* (2006.01)

(52) U.S. Cl.
CPC ............. *A61F 2/4609* (2013.01); *A61F 2/34* (2013.01); *A61F 2/4637* (2013.01); *A61F 2/4603* (2013.01); *A61F 2002/4685* (2013.01)

(58) Field of Classification Search
CPC ........ A61F 2/46; A61F 2/4603; A61F 2/4609; A61F 2/4637; A61F 2002/4681; A61F 2002/4685
See application file for complete search history.

(56) References Cited

U.S. PATENT DOCUMENTS 6,152,930 A * 11/2000 Mastrorio ............. A61F 2/4609
606/99
9,474,628 B2 * 10/2016 Gradel ....................... A61F 2/34
(Continued)

FOREIGN PATENT DOCUMENTS

CN 101478935 A 7/2009
CN 102209506 A 10/2011
(Continued)

OTHER PUBLICATIONS

"Australian Application Serial No. 2017296119, Response filed Nov. 19, 2019 to First Examination Report dated Apr. 12, 2019", 26 pages.
(Continued)

*Primary Examiner* — Eric S Gibson
(74) *Attorney, Agent, or Firm* — Schwegman Lundberg & Woessner, P.A.

(57) ABSTRACT

The present invention is directed to a system comprising a medical instrument (e.g. cup implant, 3) and a holding device (2) that interacts with said medical instrument to form a sealable cavity within the combined arrangement of components. An impaction device (1) is also provided, preferably which provides means to allow fluid to be expelled from the cavity but which prevents further fluid from entering the cavity.

20 Claims, 18 Drawing Sheets

(56) References Cited

U.S. PATENT DOCUMENTS

| | | | |
|---|---|---|---|
| 9,814,603 B2* | 11/2017 | Gradel | A61F 2/4609 |
| 10,398,570 B2* | 9/2019 | Gradel | A61F 2/4609 |
| 2005/0137603 A1 | 6/2005 | Belew et al. | |
| 2005/0228394 A1* | 10/2005 | Bihary | A61F 2/4609 606/91 |
| 2009/0248027 A1 | 10/2009 | Imhof et al. | |
| 2019/0201215 A1* | 7/2019 | Wozencroft | A61F 2/4609 |

FOREIGN PATENT DOCUMENTS

| | | |
|---|---|---|
| CN | 110072493 | 7/2019 |
| DE | 19722923 A1 | 8/1998 |
| DE | 10128234 A1 | 1/2003 |
| DE | 202007016249.9 U1 | 2/2008 |
| JP | 2019521826 | 8/2019 |
| WO | WO-2018011568 A1 | 1/2018 |

OTHER PUBLICATIONS

"Australian Application Serial No. 2017296119, Subsequent Examiners Report dated Dec. 16, 2019", 3 pages.

"European Application Serial No. 17742512.1, Communication Pursuant to Article 94(3) EPC dated Jan. 31, 2020", 5 pages.

"Japanese Application Serial No. 2019-523193, Notification of Reasons for Refusal dated Jan. 21, 2020", with English translation, 10 pages.

"International Application Serial No. PCT/GB2017/052039, International Search Report dated Sep. 29, 2017", 5 pgs.

"International Application Serial No. PCT/GB2017/052039, Written Opinion dated Sep. 29, 2017", 6 pgs.

"Australian Application Serial No. 2017296119, First Examination Report dated Apr. 12, 2019", 5 pgs.

"European Application Serial No. 17742512.1, Response filed Sep. 3, 2019 to Office Action dated Feb. 22, 2019", 13 pgs.

"Japanese Application Serial No. 2019-523193, Response filed Apr. 20, 2020 to Notification of Reasons for Refusal dated Jan. 21, 2020", with English claims, 30 pages.

"European Application Serial No. 17742512.1, Response filed Jun. 10, 2020 to Communication Pursuant to Article 94(3) EPC dated Jan. 31, 2020", 17 pages.

"Chinese Application Serial No. 201780042727.8, Office Action dated Jul. 29, 2020", with English translation, 16 pages.

"Chinese Application Serial No. 201780042727.8, Response filed Nov. 17, 2020 to Office Action dated Jul. 29, 2020", with English claims, 19 pages.

"European Application Serial No. 17742512.1, Communication Pursuant to Article 94(3) EPC dated Dec. 14, 2020", 5 pages.

"Japanese Application Serial No. 2019-523193, Final Notification of Reasons for Refusal dated Sep. 29, 2020", with English translation, 8 pages.

"Japanese Application Serial No. 2019-523193, Response filed Dec. 25, 2020 to Final Notification of Reasons for Refusal dated Sep. 29, 2020", with English claims, 26 pages.

"Chinese Application Serial No. 201780042727.8, Office Action dated Mar. 2, 2021", with English translation, 14 pages.

"European Application Serial No. 17742512.1, Response filed Apr. 22, 2021 to Communication Pursuant to Article 94(3) EPC dated Dec. 14, 2020", 25 pgs.

"Chinese Application Serial No. 201780042727.8, Response filed May 17, 2021 to Office Action dated Mar. 2, 2021", with English claims, 20 pages.

* cited by examiner

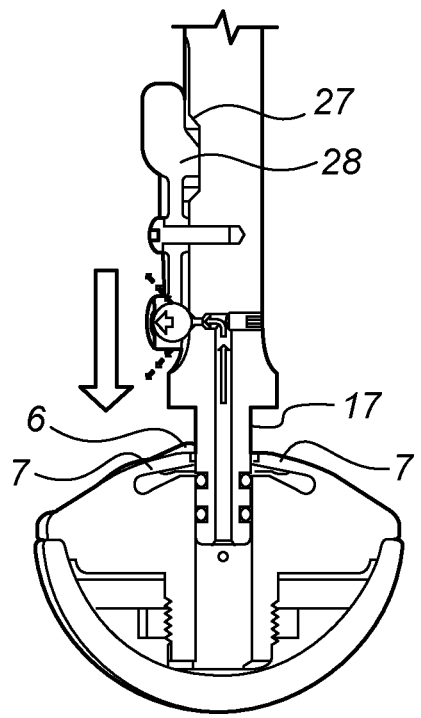
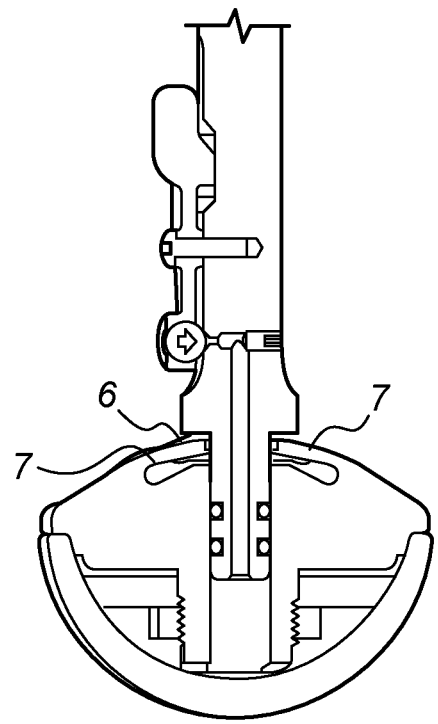
Figure 13    Figure 14
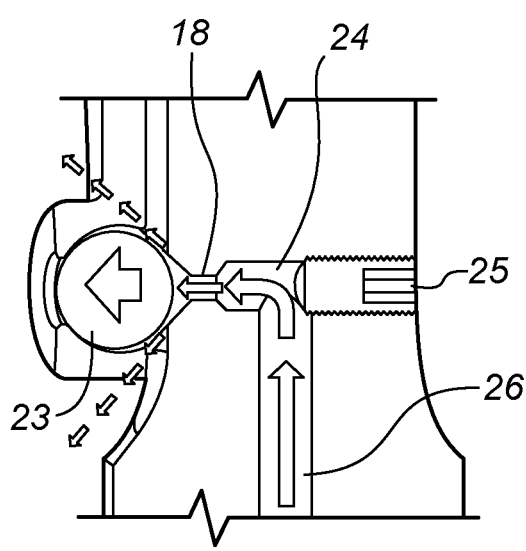
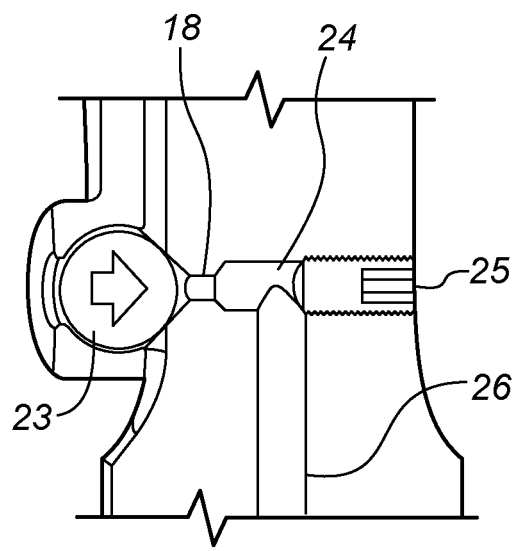
Figure 15    Figure 16

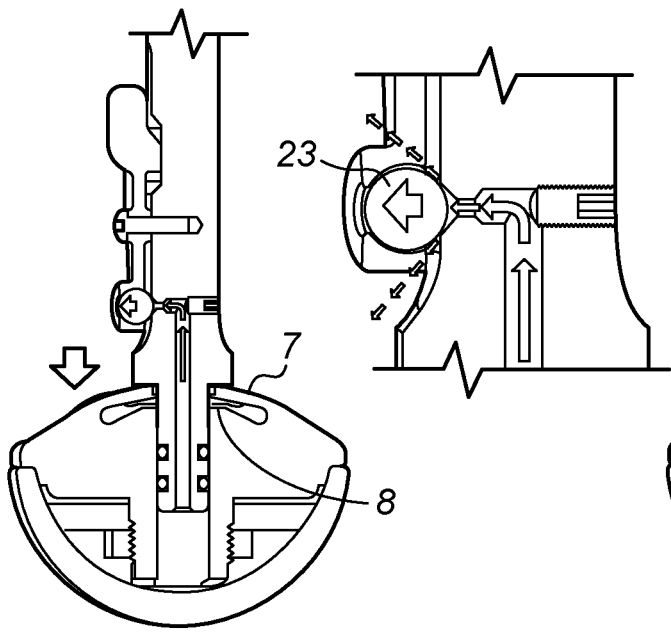
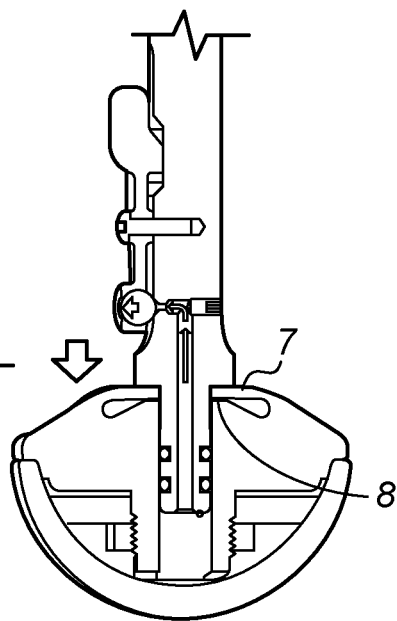
Figure 17  Figure 18
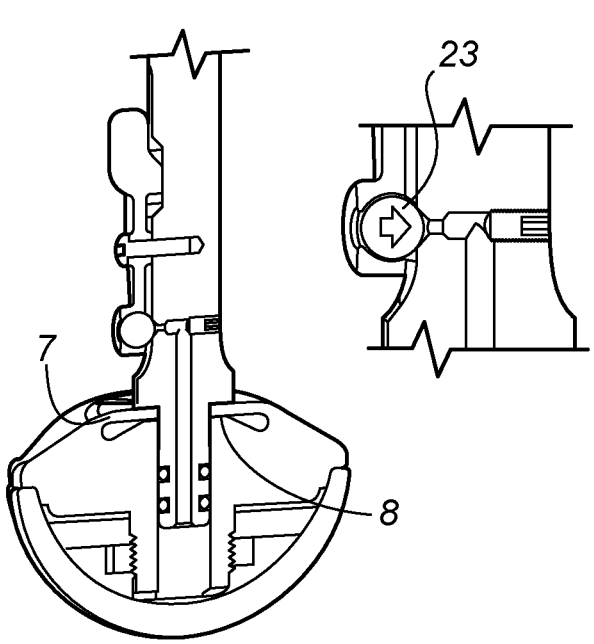
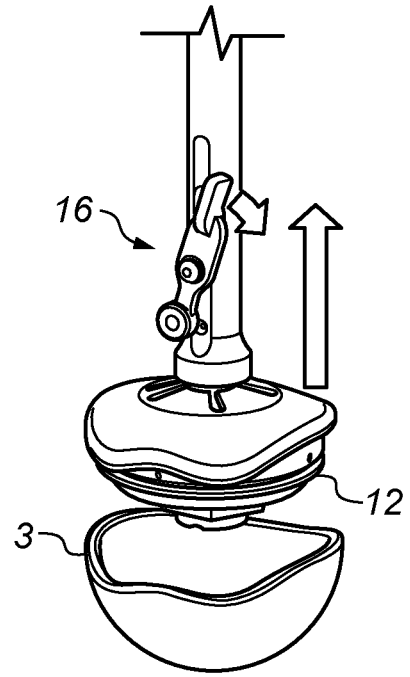
Figure 19  Figure 20

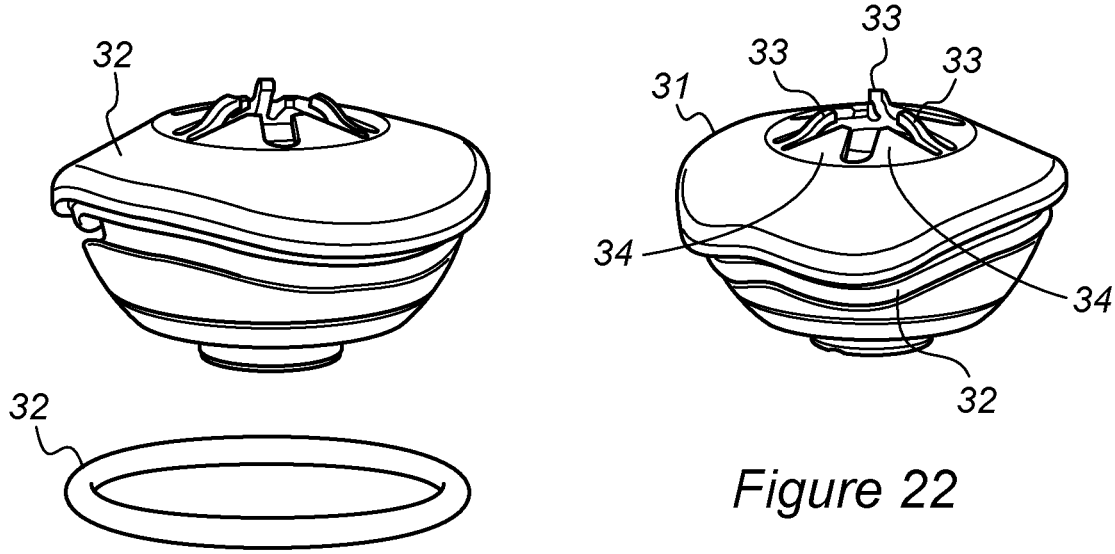
Figure 22
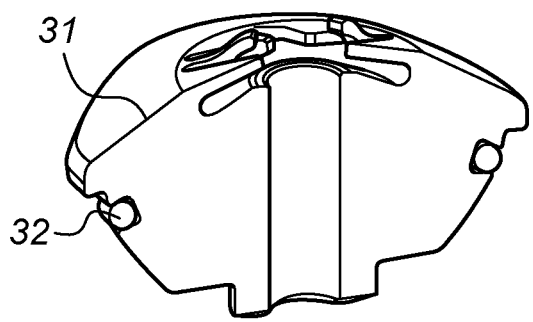
Figure 21
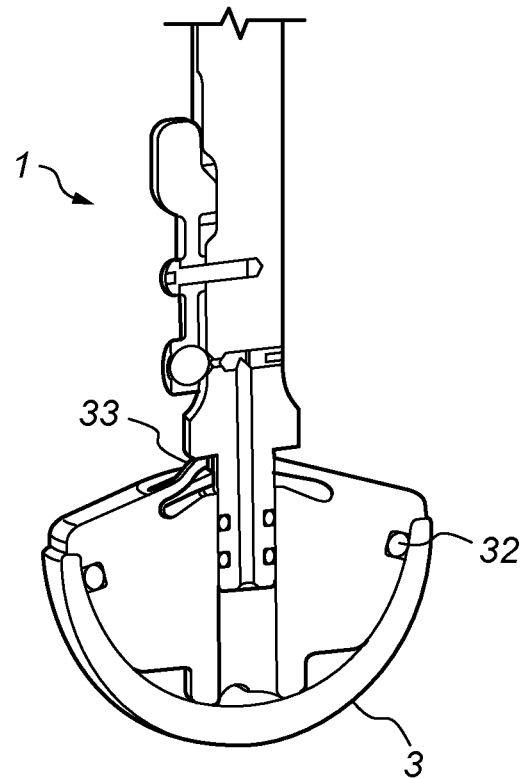
Figure 23
Figure 24

HOLDER FOR AN ACETABULAR CUP IMPLANT

This application is a U.S. National Stage Application under 35 U.S.C. 371 from International Application Serial No. PCT/GB2017/052039, filed on Jul. 12, 2017, and published as WO 2018/011568 A1 on Jan. 18, 2018, which claims priority to United Kingdom Application No. 1612056.0, filed on Jul. 12, 2016, the benefit of priority of each of which is claimed hereby, and each of which are incorporated by reference herein in its entirety.

Acetabular cup implants with large diameter bearings, such as resurfacing cups or large diameter total hip replacements (THR), are a particular challenge to hold during implantation. The surgeon must forcibly impact the cup into a prepared, slightly undersized bone socket during fitting, whilst ensuring that the cup is implanted in the correct orientation which is critical to the function of the hip implant. Furthermore, it is essential to protect the bearing surface from damage during this forcible impaction process. Most conventional THR cups consist of an outer shell and separate bearing liner which is inserted after the metal shell is implanted. Therefore the inside of the metal shell is used to provide holding features for an introducer/impaction shaft such as a screw thread or bayonet attachment. However this area is not available on resurfacing cups or cups with pre-fitted liners because the inside surface forms the bearing surface. Furthermore, the outer surface is usually fully embedded in the bone socket, so only the cup rim is accessible. Previous resurfacing designs have attempted to solve this problem in various ways, but these have resulted in compromises to the designs, either by reducing bearing arc, or reducing outer fixation surfaces or with the presence of holding features that caused snagging and aggravation of the soft tissue structures such as Psoas tendon in close proximity to the cup rim. It is now recognised that attempts by manufacturers to provide adequate cup holding solutions have a serious, deleterious effect on the clinical outcome of many resurfacing designs which have now been withdrawn from clinical use partly due to these problems.

A new generation of resurfacing implants and large diameter THR's utilising non-metal bearing materials including zirconia toughened alumina ceramic (ZTA) and cross linked ultra-high molecular weight polyethylene (UHMWPE) pose an even bigger challenge for cup holding during implantation. In the case of ZTA, due to the restraints of the manufacturing process and hardness of the material, it is technically difficult and very expensive to add small holding features that may be possible (if undesirable) in metal. Also in the case of UHMWPE, it is critical for wear characteristics and material strength that full wall thickness is maintained, so holding features that reduce wall section would be undesirable. In addition, some new generation devices are intended for specific rotational alignment of asymmetric features on the cup which also add difficulties for cup holding.

To overcome these difficulties, the present invention provides a cup holding solution without the need for special holding features on the cup and, furthermore, protects the implant bearing surface during forcible insertion.

The present arrangement comprises three elements, an impaction device or introducer assembly (introducer), a cover assembly (cover) and a cup implant (cup). A holding grip is established between the three elements by means of a fluid in a sealed cavity under low pressure. The sealed cavity is established by means of two seals and a non-return valve. One seal is made between the introducer and the cover and the other seal is made between cover and the cup. The non-return valve is incorporated in the introducer and forms an outlet for air and surplus fluid to escape from the sealed cavity as the three elements are pressed together (whilst preventing fluid or air re-entering the cavity).

The fluid used to fill the sealed cavity is preferably any liquid which is freely available in the operating theatre (e.g. sterile water. Variants of sterile water include Ringers solution, saline solution etc.). This is typically chilled, although can also be at ambient temperature. The fluid is introduced by pouring it in and filling the cup as it rests upright in the opened packaging or on a sterile surface. Next the cover is inserted onto the cup and finally the introducer is inserted into the cover. Filling the cup provides a surplus of fluid, so that air at the surface is first expelled from the cavity via the non-return valve followed by surplus fluid.

In one arrangement, the low pressure in the fluid is achieved by means of a resilient feature on the cover adjacent to a flange on the introducer attachment which flexes down and in so doing reduces the volume of the sealed cavity. Low pressure is maintained because the resilient feature is flexed within its elastic limits and tries to forcefully return to its un-flexed state thereby holding the fluid at low pressure. The low pressure state of the fluid pulls together all three elements forming a tight fit between them and making the overall assembly feel rigid. Any force exerted between the introducer and the cup is automatically directed through the resilient feature due to its position on the cover adjacent to the introducer attachment. The resilient feature is a method to transfer mechanical force to fluid suction and can be achieved in a variety of alternative ways with integral features in the cover or additional parts such as Belleville washers.

The resilient feature on the cover preferably comprises at least one fin or finger. Preferably it comprises one or more light flexing fingers and stiffer flexing fingers. The light flexing fingers are raised up higher and therefore engage with the introducer flange first and require only light force to press them down until level with the stiffer flexing fingers. Then all flexing fingers act together and require greater force to press them down to the position where they bottom out against a solid part of the cover.

In use the resilient feature has a light flexing stage (stage 1), a stiffer flexing stage (stage 2) both reduce the volume of the sealed cavity. Stage 2 results in the resilient features bottoming out completely. Initially in stage 1, a hold is achieved between the three elements by pressing them together with light manual force. This hold is sufficient to manipulate the cup into position in the patient's hip socket. However once the surgeon impacts the introducer with the hammer blows required to achieve the jam fit of the cup into the hip socket, the resilient feature enters stage 2 (the stiffer flexing stage). This further reduces the volume of the sealed cavity and due to the increased stiffness of the resilient feature (which is still within elastic limits and tries to return to its un-flexed state with considerable force) it increases the strength of the hold between all 3 elements. As the resilient feature has reached the end of its travel (bottomed out) it holds that position under the low pressure fluid seal. When fully bottomed out, the cap has the stiffness of a solid part so that the force of the hammer blows is more efficiently transferred to jam fitting the cup.

It is desirable to have a stronger hold as the cup is impacted because it may veer out of alignment as the jam fit increases or the surgeon may wish to adjust alignment as the cup advances toward full seating. Furthermore it is desirable for the cover to regain the stiffness of a solid part (stage 2)

so that the force of the hammer blows is transferred efficiently to where it is needed and the surgeon can maintain feel and detect when the cup is fully seated.

Once the cup is fully inserted into the hip socket, the low pressure fluid seal is released by manually opening a non-return valve.

Another way to describe the mechanism of achieving the hold between introducer, cover and cup is that the fluid is maintained under suction (instead of low pressure) in the sealed cavity. Therefore fluid suction pulls together all three elements forming a tight fit between them and making the overall assembly feel rigid. The suction is increased as the resilient feature flexes from stage 1 to stage 2 and the suction is released by manually opening the non-return valve.

Given that liquids exhibit both adhesion forces (a tendency in liquids to cling to a surface on which it rests) and cohesion forces (a tendency within a liquid to resist separation), it is not essential to incorporate the resilient feature to reduce the volume of the cavity and lower pressure in the liquid as described previously and illustrated in FIGS. 1-4, 10-14, 17-24 and 27. Without such a resilient feature, and provided a sealed cavity for the liquid is maintained, a holding force will be established between the different elements of the device due, jointly, to the adhesive/cohesive forces in the liquid and the seal and a valve preventing air from entering the cavity of liquid. These holding forces can be capitalised by having maximum surface area between the holding elements and maximum surface congruency with a uniform small gap in-between. This applies particularly to the cover assembly and cup implant.

Thus, in an arrangement that can be cumulative to a cover comprising a resilient feature, or as an alternative to a cover comprising a resilient feature (i.e. where no resilient feature is present), there is present a cover assembly which interacts with an impaction device. The impaction device comprises a proximal end, a shaft, and a distal region that interacts with at least a part of said cover assembly, said shaft and/or distal region of said impaction device further comprising a mechanism that prevents additional fluid from entering the cavity that is created within the resulting combination of the cup, cover assembly and impaction device.

The mechanism that prevents additional fluid from entering the cavity is preferably a releasable non-return valve. Such a valve allows air and excess liquid to escape during the pressing together stage, and (when opened) to enable air to enter the cavity to reduce the holding forces so that the cup implant can be released once positioned correctly in the body. Furthermore, because it is sometimes difficult to capitalise adhesive/cohesive holding forces between the Introducer and the cover due to there being less surface area available to take advantage of adhesive/cohesive forces, a mechanical locking feature may also be employed to capitalise the maximum amount of hold between all three elements.

Those skilled in the art will appreciate that it is desirable to operate such a system with liquid fluid as opposed to air because such fluids are relatively incompressible compared to gases. This is the fundamental reason why hydraulics are used as source of mechanical force or control where high forces are required and pneumatics are used as source of mechanical force or control where low forces are required. It follows that, as fluids are relatively incompressible compared to gases under high pressure, the same is true in reverse under low pressure (suction or tension) they are relatively un-expandable compared to gases. It is therefore the case that, with the present invention, much higher holding forces are possible when (sterile) water is used and it is desirable to exclude all air (or as much air as a possible) from the sealed cavity. Any air remaining in the cavity will reduce the holding force and introduce a 'spongy' feel much like where air leaks into a hydraulic brake system on a vehicle. The features of all three elements and method of assembly are designed to expel all air and leave only sterile water in the sealed cavity However it is a feature of the current invention that, although the holding force typically is not as great, it will function with air instead of liquid (e.g. water). Therefore it is not mandatory to introduce sterile water, it can be a matter of choice for the surgeon. Although this is not as desirable, because the advantages of maximum holding force are several fold, the function can be described as generally the same as above except that the hold is achieved by having a partial vacuum in air, or alternatively low pressure in air, or alternatively suction in air (instead of low pressure or suction in water).

Preferably, the cover is single use and consists of three parts manufactured in a plastic material such as nylon, and a seal made from a softer material such as silicone. However in an alternative embodiment, the cover consists of a single plastic part and an O-ring seal. The cover may be supplied with the implant or separately within an instrument set. Preferably the introducer is single use and consists of long shaft manufactured in a metal such as aluminium alloy and peripheral parts forming the seals and non-return valve and means of fixing them together. The metal shaft is intended to transfer force from hammer blows outside the surgical site to forcibly insert the cup in the patient's hip socket.

The cup shown in the following drawings is a contoured resurfacing cup, however the present invention could be used with any type of acetabular cup implant made either from one piece or 2-part pre-fitted with a bearing liner. Those skilled in the art will appreciate there are many different types of hip cup implant for resurfacing and total hip replacement (THR). Resurfacing cup implants include mono-block cups manufactured from ceramic, metal and plastic material, either with circular (planar) rim or contoured rim. THR cup implants include the options above, plus metal outer shell with either ceramic, plastic or metal bearing inserts, either with circular (planar) rims or contoured rims. The function of the present invention only relies on a smooth bearing surface to make a seal which is common to all of the above options as all cup bearings must be very smooth and highly finished, therefore its application extends to all hip cups implants.

In one embodiment of the present invention there is provided a system comprising:

(i) a medical instrument and a holding device that interacts with said medical instrument or that interacts with an insert positioned in/on said medical instrument, wherein the interaction between the medical instrument and/or insert and the holding device creates a cavity within the resulting combination of said medical instrument and/or insert and said holding device which cavity is at least partially filled with fluid, wherein the holding device comprises a cover assembly for placing into said medical instrument and/or insert, said cover assembly comprising:

a proximal surface, said proximal surface comprising a region that is able to interact with or receive an impaction device;

a distal surface located away from the proximal surface of the cover assembly and arranged to fit in said medical instrument and/or insert, said distal surface comprising at least a seal; and (ii) an impaction device, said impaction device comprising:
a proximal end;
a shaft; and
a distal region that interacts with at least a part of said cover assembly,
said shaft and/or distal region of said impaction device further comprising a mechanism that prevents additional fluid from entering the cavity.

In one arrangement, the mechanism that prevents additional fluid from entering the cavity can be a one-way valve. The one-way valve can be located at any suitable point on the impaction device—for example along the shaft, and/or in the distal region/tip/end of the impaction device. The one way valve is typically in fluid communication with the cavity of the medical implant/holding device and the outside atmosphere. Where the valve is located on the shaft, then there is a channel that extends from the valve port (exit port) to and through the distal end of the shaft in order to link the cavity with the valve. Where the valve is located at the distal region of the shaft (e.g. within the tip of the shaft, and/or protruding from the tip of the shaft to interact with a hole or the cavity in the cover assembly), then it is preferably that there is a channel in the shaft allowing fluid to be expelled. However, the presence of a channel in such an arrangement is not an essential requirement. Any excess fluid in such cases can be expelled by being forced through the seal that the cover assembly makes with the surface of the implant/insert.

In one arrangement, the distal region of said impaction device comprises a pin, said pin being operable to releasably seal said cavity. The sealing of the cavity can be achieved by many different arrangements. Preferably, a portion of the pin is profiled to fit into a complementarily profiled portion of a hole that extends through the cover assembly. The skilled person will appreciate that there can be many types of profile that can achieve the desired effect. For example, the pin can culminate at a pointed end, for example having at least a partially conical profile. The hole in the cover assembly can have a complementary shaped region which accepts the pin to afford a sealing fit. Other arrangement might include the pin having a convex or spherical end profile, which fits into a concave or spherical hole profile. Alternatively, the end of the pin may have a cylindrical profile which may optionally comprise an additional seal (such as an o-ring or the like).

The portion of the hole in the cover assembly that interacts with the pin may comprise a varied profile throughout its length from the distal surface toward the proximal surface. For example, the main portion of the hole may be of a cylindrical profile, with only the proximal end being shaped to receive a sealing pin.

The diameter of the hole extending through the cover assembly may also be varied. For example, in a distal region of the cover assembly, the hole may be of relatively small diameter. This may change gradually (e.g. with a tapered profile) or abruptly into a wider diameter hole, for example in order to be wide enough to receive the distal end of the impaction device.

There may be an additional seal surrounding the channel of the cover assembly at a position where the channel widens to accept the impaction device. The distal end of the impaction device may be seated on this seal when inserted into the cover assembly. The pin may then extend from the distal end into a valve seating of the channel.

In some arrangements, the distal region of the impaction device further comprises a locking mechanism which interacts with said holding device in order to assist in maintaining secure connection between said impaction device and said holding device.

In some arrangements, the distal region of said impaction device comprises a pin, said pin being operable to releasably seal said cavity, and said pin interacts with the locking mechanism in order to allow or prevent the locking mechanism to interact with said holding device to effect locking and unlocking, respectively, of the impaction device to the holding device.

In one arrangement there is provided a system comprising a medical instrument and a holding device that interacts with said medical instrument, wherein the interaction between the medical instrument and the holding device creates a cavity between said medical instrument and said holding device, said holding device comprising means to allow the cavity to be sealed, said system comprising:
a) means to create a low pressure or suction within the cavity;
b) means to maintain said low pressure or suction.

The medical instrument will preferably be a cup implant. In certain preferred arrangements, the implant is a hip implant. Such implants will typically have a smooth concave surface, which in use will interact with a ball implant to create a ball and socket joint. The smooth concave surface is helpful in being able to form a seal with the holding device. A seal is important as this allows the creation of a low pressure environment, or a suction force, to be generated within the cavity between the medical instrument (e.g. cup implant) and the holding device.

There are a number of means to create a low pressure or suction within the cavity, as will be discussed in more detail herein. Once such means is in the configuration of the holding device itself. This can comprise a cover assembly which has a resilient and elastically deformable portion on it which acts to create a low pressure or suction in the cavity by e.g. biasing the cover assembly away from the implant (e.g. if the resilient portion is on the distal side of the cover assembly in contact with the concave surface of the implant) and/or biasing an introducer device (impaction device) away from the cover assembly after the impaction device has been connected to the cover assembly (e.g. if the resilient portion is on the promixal side of the cover assembly away from the concave surface of the implant and in contact with the impaction device).

In additional or alternatively, the holding device can comprise e.g. a plunger mechanism. This is typically associated with the impaction device so as to be in fluid communication with a channel associated with the impaction device and in fluid communication with the cavity formed between the cover assembly and the medical instrument (e.g. implant). In this manner, by withdrawing the plunger, fluid is "sucked" away from the cavity and towards the plunger mechanism, thus creating a low pressure or suction within the cavity in light of the seal formed between the cover assembly and the implant. Many different arrangements can be foreseen by the skilled person. For example, the plunger could comprise a screw fixing associated with the impaction device, whereby unscrewing the plunger "sucks" liquid towards it and vice versa. Alternatively, there may be a plunger arrangement whereby a lever associated with the impaction device is used to pull out the plunger. Alternatively there may be a syringe-like structure that is associated with the impaction device, which again acts to suck fluid away from the cavity.

In further arrangements, there is provided a system which further comprises:

c) means to reduce cavity volume from its initial volume, said initial volume being the volume of said cavity when the holding device is inserted into said medical instrument to a predetermined position;

d) means to maintain said reduced cavity volume.

By initial volume being the volume of said cavity when the holding device is inserted into said medical instrument to a predetermined position, it is meant that the cover assembly of the holding device will be placed into the medical instrument (cup implant) during initial set up of the system. This will usually be after a liquid has been added to the implant. Thus, on initial insertion, there will be displacement of the fluid in the cup implant as the cover assembly moves into the space previously occupied by the fluid. Once the cover assembly has reached a predetermined position on the initial set up, this is deemed to set the "initial volume" of the cavity. The predetermined position may be e.g. when the cover assembly interacts with the rim of the medical device such that the body of the cover assembly can no longer be pushed into the implant. Or it may be the position when the seal on the cover assembly has full contact with the wall of the implant. This will typically occur prior to the cover assembly being fully inserted into the implant. Thereafter, the cavity volume can be manipulated and reduced by various means as described herein.

The means to reduce cavity volume from its initial volume may be via a resilient and elastically deformable portion on the holding device cover assembly. Such portion, if e.g. positioned on the distal side of the cover assembly, will allow the cover assembly to be pushed further into the implant after its initial insertion to further reduce the cavity volume. Likewise, if the resilient portion is on the proximal surface of the cover assembly, then on insertion of the impaction device the resilient portion will allow the impaction device to be inserted further into the cavity (which includes any hole extending through the cover assembly from the distal side to the proximal side) by being elastically deformed towards the distal end. The part of the impaction device that is situated in the through-hole of the cover assembly will therefore move towards the distal end of the cover assembly within the hole, thereby displacing any fluid in the hole and effectively reducing cavity volume.

The means to maintain said reduced cavity volume can be e.g. by the seal and resultant suction effect, which does not allow the arrangement to revert to its initial and relaxed position.

In preferred embodiments of the present system, said system further comprises a fluid, said fluid being introduced to said system such that said fluid is present in said sealed cavity. Preferably said fluid is liquid and there is no or substantially no gas present in said sealed cavity after the cover assembly has been inserted into the implant and any excess liquid and gas has been removed. An advantage of liquid over gas arises from the relative incompressability of liquid. Preferably the fluid is introduced prior to the cover assembly being placed into the implant. This may reduce the risk of gas being trapped in the cavity.

In some arrangements, a kit can be provided comprising an implant, a cover assembly, an impaction device and a container of liquid.

Preferably, the system will also comprise means to release fluid low pressure or suction.

This may be in the form of a valve associated with the impaction device, whereby when the valve is activated it effectively breaks the seal between the cavity and the outside atmosphere and the pressure in the cavity equilibrates. Such valve is typically a one way valve, such as a ball valve or an o-ring, which may allow fluid to escape from the cavity but prevents any gas or liquid from entering the cavity. Alternatively, or in addition, the cover assembly may have a plug or valve associated with it, whereby the seal can be broken via the cover assembly. In some instances, the cover assembly may have a predrilled hole extending from the distal region towards the proximal surface, and drilling through the proximal surface to reach the hole will break the seal.

In some arrangements, the system can further comprise:
means to introduce fluid to said cavity; and/or
means to expel surplus gas and/or liquid.

Preferably the means to introduce fluid is by pouring the fluid into the concave cup implant beforehand. Fluid can be poured into the concave cup cavity from a bottle, beaker, phial or syringe. Filling the cup completely provides a surplus quantity of fluid which is beneficial to ensure that all air is expelled from the cavity during assembly of the cover and introducer so that only fluid remains in the sealed cavity. Surplus liquid is expelled during assembly of the cover in the cup implant by overflowing over the rim of the cup implant and/or through the hole in the cover. Additional surplus gas and/or liquid is expelled through the non-return valve as the introducer is assembled into the cover.

In some preferred arrangements, the system comprises a holding device which comprises a cover assembly for placing into said medical instrument, said cover assembly comprising:
a proximal surface, said proximal surface comprising a region that is able to interact with an impaction device;
a distal surface located away from the proximal surface of the cover assembly and arranged to fit in said medical instrument, said distal surface comprising at least a seal.

In certain arrangements, it may not be necessary to have a resilient portion associated with the cover assembly to act as a means to create a low pressure/suction or to reduce cavity volume. This, for example, could be created by alternative means, such as a plunger mechanism as discussed herein.

In other arrangements, however, the cover assembly further comprises:
at least one resilient and elastically deformable region associated with the cover assembly such that when elastically deformed in a stressed state there is natural bias of the resilient and elastically deformable region to revert to its unstressed state.

As described above, this is one arrangement by which the means to create a low pressure or suction within the cavity can be effected. Likewise, this is one arrangement by which the means to reduce cavity volume from its initial volume can also be effected.

The resilient and elastically deformable region can be, or can be associated with, a portion of the proximal surface of the cover assembly. This arrangement can be preferred when an impaction device is used which is in fluid communication with the cavity between the cover assembly and the implant.

Alternatively, or in addition, the resilient and elastically deformable region can be, or can be associated with, a portion of the distal surface of the cover assembly. Such an arrangement may be preferred when the impaction device is not in fluid communication with the cavity.

In some arrangements, the resilient and elastically deformable region is formed integrally with the cover assembly.

In some arrangements, the resilient and elastically deformable region is formed from a portion of material extending from the cover assembly. This can either be of the same material as that of the cover assembly, or it may be a different material from the respective surface of the cover assembly. In some arrangements, there may be a mixture of same and different material as that of the cover assembly.

In some arrangements, the portion of material extending from the cover assembly comprises at least one finger or fin. This will typically be made by one or more cuts in the material between fins, thereby creating fins of material between the cuts.

Preferably, the at least one fin comprises a plurality of fins, one or more of said plurality of fins being of substantially the same dimensions. Alternatively or in addition the at least one fin comprises a plurality of fins, one or more of said plurality of fins being of differing dimensions.

In preferred arrangements, there are a plurality of thin fingers/fins and a plurality of thick fingers, relative to one another. One or more fingers (preferably one or more thin fingers) can optionally extend above the plane of the one or more thicker fingers, such that they interact with the impaction device (if on the proximal surface) or with the cup implant (if on the distal surface) prior to the thicker fingers making contact.

In addition, or alternatively, the resilient and elastically deformable region can comprise one or more springs, one or more washers (e.g. Belleville washers), or a combination of springs and washers.

In preferred embodiments, the cover assembly is structured such that at least a portion of the resilient and elastically deformable region is able to reach a stop when under stress and prior to loss of elastic deformation, the stop forming a platform whereby the resilient and elastically deformable region effectively forms a non-moving unit with the main body of the cover assembly such that force is able to be transmitted efficiently throughout the resilient and elastically deformable region and main body of the cover assembly.

The stop forming the platform which the resilient and elastically deformable region contacts when under stress can be suitably spaced from the resilient and elastically deformable region, such that the portion of the resilient and elastically deformable region that comes into contact with the platform does so prior to any plastic deformation resulting in loss of bias to the unstressed state.

As discussed above, in some preferred arrangements and particularly where an impaction device is used which comprises a channel in fluid communication with the cavity, the cover assembly comprises a hole extending from and through the proximal surface to and through the distal surface.

As also discussed above, the cover assembly can further comprise a hole in the distal surface beyond the seal, said hole extending into the cover assembly but not penetrating through the proximal surface. This hold is designed to be accessed from the proximal side of the cover assembly (e.g. via drilling, or via a pre-formed removable plug) so as to break the seal between the cavity and the external atmosphere.

In certain arrangements, the cover assembly can comprise multiple parts which fit together to form the cover assembly, said multiple parts comprising:
- a first part comprising at least said proximal surface, optionally also comprising said distal surface;
- optionally a second part comprising said distal surface;
- a seal; and
- means for securing said seal to said first and/or second part.

In further arrangements of the system, the system further comprises an impaction device, said impaction device comprising a part that interacts with at least a part of said cover assembly.

In some arrangement, the impaction device does not need to have a channel in fluid communication with the cavity. This is particularly so in arrangements where the cover assembly is structured so as to be useable with a solid impaction device.

Preferably, however, the impaction device comprises:
- a proximal end;
- a shaft; and
- a distal region containing a channel, said channel comprising an entry port at the distal end/tip of said distal region and an exit port at a point on the shaft away from the distal end/tip, said impaction device further comprising means to removably block the exit port.

By this arrangement, there is provide one example of means to means to create a low pressure or suction within the cavity and to maintain said low pressure or suction.

Preferably, the means to removably block the exit port is a non-return valve. This can optionally be e.g. a ball valve and/or an o-ring or the like.

As discussed, in arrangements where the impaction device comprises a channel designed to be in fluid communication with the cavity between the cover assembly and the implant, the cover assembly of the holding device comprises a hole extending from and through a proximal surface to and through a distal surface of the cover assembly, at least a portion of said hole dimensioned to receive a portion of said impaction device.

The impaction device can comprise a flange in the distal region, said flange being able to interact with the holding device to stabilise the siting of the impaction device on or in the holding device.

Again, as discussed herein, in some arrangements the impaction device further comprises a mechanism to create a low pressure or suction within the cavity, such as by use of a plunger in communication with said channel, said plunger being adjustable to draw or push the fluid within the channel and hence in said cavity.

In use, it is a preferred arrangement that when suitable pressure is exerted on the impaction device, such pressure permits the elastic deformation of at least a portion of the resilient and elastically deformable region towards the distal surface of the cover assembly.

Preferably, the cover assembly is structured such that at least a portion of the resilient and elastically deformable region is able to reach a stop when under stress, the stop forming a platform whereby the resilient and elastically deformable region effectively forms a non-moving unit with the main body of the cover assembly such that force is able to be transmitted efficiently throughout the resilient and elastically deformable region and main body of the cover assembly and wherein further elastic deformation of the portion of the resilient and elastically deformable region is prevented by the stop.

It should be recognised that although a system has been described herein comprising an implant, a holding device and an impaction device, the holding device and the impaction device can be considered as separate entities that can be provided independently of the system and can be modified in themselves to a degree which still allows the system to function to achieve the inventive aspect of the invention.

There is also provided herein a method of holding a medical instrument (implant) using a fluid, preferably a liquid, the fluid being introduced to the medical implant and the medical implant thereafter being capped with a holding device, the holding device comprising a cover assembly arranged to displace excess fluid from the cavity formed between the medical implant and the cover assembly and to form a seal, the holding device thereafter being manipulated in order to create a suction force within the cavity and to maintain said suction.

Such manipulation can further comprise reducing the cavity volume from its initial volume, said initial volume being the volume of said cavity when the holding device is inserted into said medical instrument to a predetermined position, and maintaining said reduced cavity volume.

The holding device can comprise a cover assembly comprising a resilient and elastically deformable region, said manipulation of said cover assembly acting on at least a portion of said resilient and elastically deformable region to reduce the volume of the cavity, the resilient and elastically deformable region thereafter being prevented from returning to a relaxed state resulting in the reduction of pressure of fluid within the cavity.

The method can comprise the steps of:
(a) introducing fluid, preferably a liquid, to a cavity of said medical implant;
(b) introducing said cover assembly of said holding device into said cavity of said medical implant, said cover assembly displacing excess fluid present in said cavity and forming a first seal between said cover assembly and said medical implant.

The method can further comprise the steps of:
(c) introducing an impaction device to said cover assembly;
(d) further fluid from said cavity being removed.

The method can further comprise the steps of applying pressure to said impaction device to elastically deform at least a portion of the resilient and elastically deformable region of said cover assembly, the deformation resulting in a further reduction in the available cavity space of the medical implant and the displacement of further fluid from said cavity.

The method can further comprise the step of:
(e) applying further pressure to said impaction device such that said resilient and elastically deformable region contacts a stop on the cover assembly, said stop forming a platform that prevents the resilient and elastically deformable region from plastic deformation resulting in loss of bias to the unstressed state, and furthermore allows force is able to be transmitted efficiently throughout the resilient and elastically deformable region and main body of the cover assembly.

Preferably, the method comprises use of the system as described herein.

The method can further comprise the step of creating a breach in the seal between the medical implant and the holding device in order to release the holding device from the medical implant.

An example of the invention will now be described by referencing to the accompanying drawings:

FIG. 1 is an exploded view showing all 3 elements, introducer assembly (introducer), cover assembly (cover) and cup implant (cup).
FIG. 2 shows the cover from above.
FIG. 3 is a cross sectioned view of FIG. 2.
FIG. 4 is an exploded view of the holder.
FIG. 5 shows the full introducer.
FIG. 6 is a cropped view of the introducer with the non-return valve in the open position.
FIG. 7 is a cross sectioned view of the cropped introducer with the he non-return valve in the closed position.
FIG. 8 is an exploded view of the cropped introducer.
FIG. 9 shows the cup resting in a flat surface being filled with sterile water from a bottle.
FIG. 10 is an exploded showing the cup filled with water and cover about to be inserted.
FIG. 11 is a cropped view of the introducer with the non-return valve being manually closed.
FIG. 12 is a cross sectioned view of the cover assembled on the cup with the introducer about to be inserted.
FIG. 13 is a cross sectioned view of the cover assembled on the cup with the introducer partially inserted.
FIG. 14 is a cross sectioned view of the assembled device with the cover resilient feature in an initial position but not pressed down.
FIG. 15 is a close up cross sectioned view of the non-return valve opened by water flowing through it.
FIG. 16 is a close up cross sectioned view of the non-return valve closed to prevent water or air returning to the internal cavity.
FIG. 17 is a cross sectioned view of the assembled device with the cover resilient feature pressed down partially by manual force (stage 1).
FIG. 17 (inset) is a repeat of FIG. 15 to indicate that non-return valve is opened by water flowing through it in FIGS. 17 & 18.
FIG. 18 is a cross sectioned view of the assembled device with the cover resilient feature pressed down fully by impaction hammering forces (stage 2).
FIG. 19 is a cross sectioned view of the assembled device with the cover resilient feature held in the fully pressed down position by the low pressure water in the internal cavity (maximum holding force).
FIG. 20 shows the released cup following manual opening of the non-return valve
FIGS. 21-24 show an alternative embodiment of the cover:
FIG. 21 is an exploded view of the alternative cover.
FIG. 22 is the assembled alternative cover.
FIG. 23 is a cross sectioned view of the assembled alternative cover.
FIG. 24 is a cross sectioned view of the alternative cover assembled with introducer and cup (equivalent to FIG. 14 with preferred cover above).
FIGS. 25-28 show an alternative embodiment of the introducer (1):
FIG. 25 shows the full alternative introducer.
FIG. 26 is a cropped view of the introducer with the non-return valve in the closed position.
FIG. 27 is a cross sectioned view of the introducer with the non-return valve in the open position.
FIG. 28 is a close up view of FIG. 27.
FIG. 29 shows the assembled device as the cup implant is inserted into a patient's hip socket (hammer not shown).
FIGS. 30-32 show three further alternative embodiments of the introducer:
FIG. 30 is a cross sectioned view of alternative introducer (2).
FIG. 31 is a cross sectioned view of alternative introducer (3).
FIG. 32 is a cross sectioned view of alternative introducer (4).
FIGS. 33-35 show an alternative embodiment of the cover and introducer:
FIG. 33 is an exploded view of the three device elements (cup implant, cover and introducer).

FIG. 36 is an exploded view of the cover component parts.

FIG. 37 is a cross sectioned view of the assembled cover.

FIG. 38 is an exploded view of the alternative introducer.

FIG. 39 is an exploded view the three device elements (cup implant, cover and introducer).

FIG. 40 is a cross sectioned view of the cup implant and cover being positioned together.

FIG. 41 is a cross sectioned view of the cup implant and cover fully positioned together.

FIG. 42 is a cross sectioned view of the three elements assembled together with valve closed.

FIG. 43 is a cross sectioned view of the three elements assembled together with valve opened.

FIG. 44 is a cross sectioned view of the introducer and cover partially dis-assembled.

Figure 1:
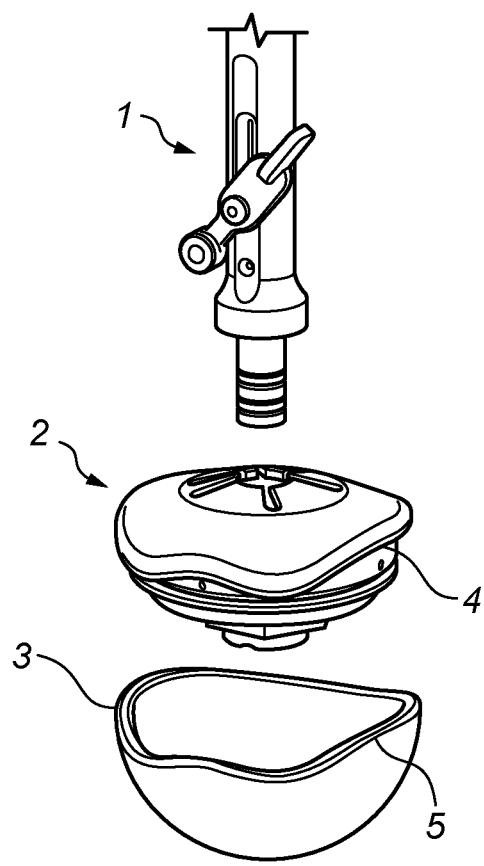

FIG. 1 shows all 3 elements, introducer assembly (introducer) [1], cover assembly (cover) [2] and cup implant (cup) [3]. It can be seen that the contoured rim [5] of the cup matches the contoured flange [4] of the holder. In some embodiments, however, the rim and flange will be flat instead of contoured and the cup implant may consist of 2 or more parts. Furthermore spigot [17] on introducer [1] fits aperture [9] on the holder [2] so that all three elements fit together in use.

Figure 2:
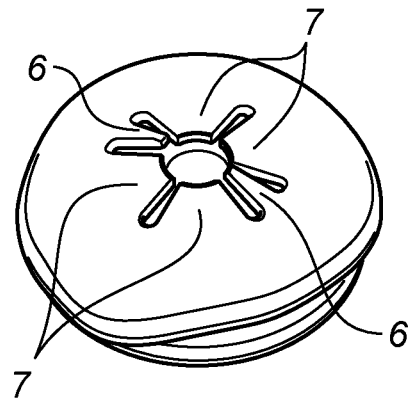
Figure 3:
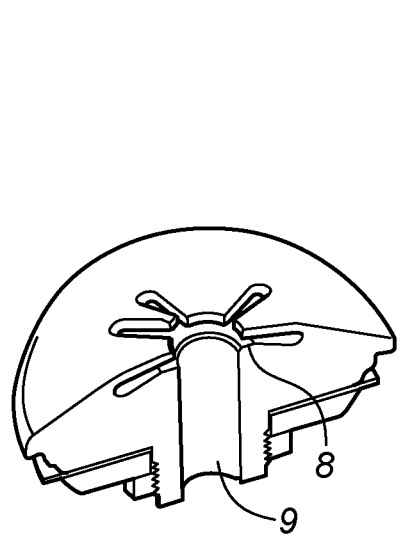
Figure 4:
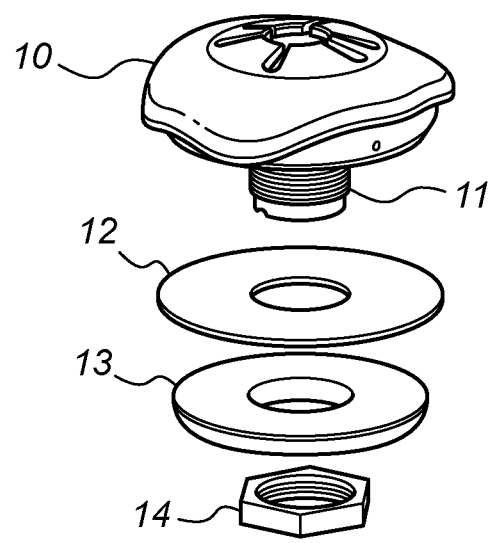

FIGS. 2-4 show the holder. Preferably, the holder is single use. The holder may be supplied assembled with the implant or separately with the instruments. It can be seen in FIGS. 3-4 that this embodiment of the holder consists of 4 parts, body [10], seal [12], washer [13] and nut [14]. When tighten together with the nut on screw thread [11] of the body [10], the seal is sandwiched tightly between adjacent surfaces on the body and washer as shown in FIG. 3. The body, washer and nut are preferably manufactured in plastic (such as nylon) which will not damage the hard implant bearing surfaces. Preferably, the holder is manufactured by an additive manufacturing process. The skilled person is aware of a number of different types of additive manufacturing processes, for example selective laser sintering (SLS) or stereolithography (SLA). Alternatively these parts could be moulded in plastic, for example by injection moulding or cold curing casting resin. Alternatively they could be manufactured in plastic by any other means, including machining. The seal [12] is a flat disc with central hole and is manufactured from a soft material such as silicone, which flexes to conform to the cup bearing surface to make a watertight/airtight seal. Alternatively the seal could be manufacture in nitrile rubber, thermoplastic elastomer (TPE), or polyurethane. Preferably the seal is die cut from sheet material.

In FIGS. 2 & 3, the integral resilient feature on the cover body is shown, consisting of 2 light flexing fingers [6] and 4 stiffer flexing fingers [7]. The light flexing fingers are raised up higher and therefore engage with the introducer flange [19] first. Also visible in FIG. 3 is the solid part of the cover body [8] which the flexing fingers [6&7] bottom out onto in use.

FIGS. 5-8 show the introducer with integral non-return valve [16]. It can be seen from FIGS. 7 and 8 that this embodiment of the introducer consists of 7 parts, shaft [15], 2 O-ring seals [20], valve body [21], valve ball [23], headed screw [22] and set screw [25]. The 2 identical O-ring seals [20] and ball valve are manufactured from a soft material such as silicone, which conforms to make a seal with mating surfaces. Alternatively they could be manufactured in other soft materials such as nitrile rubber, thermoplastic elastomer (TPE), or polyurethane. The valve body [21] is preferably manufactured in plastic (such as nylon) by an additive manufacturing process. The two screws [22&25] are standard parts manufactured in either metal or plastic.

Figure 5:
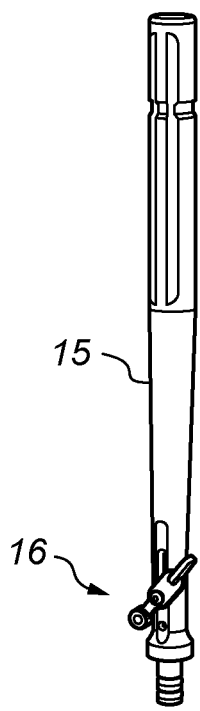
Figure 6:
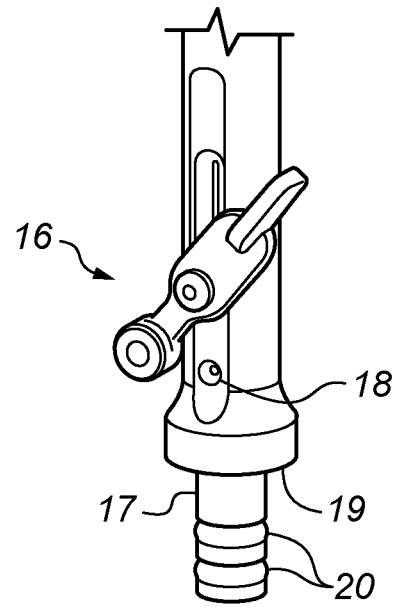
Figure 7:
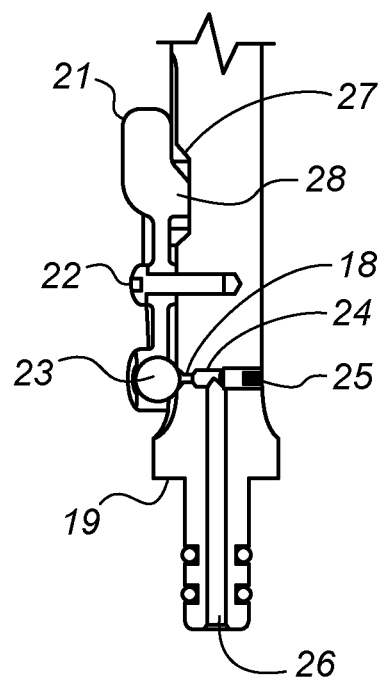
Figure 8:
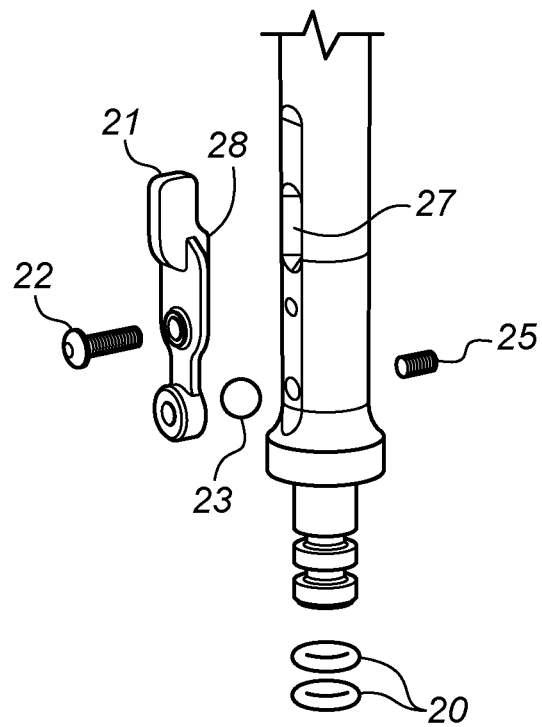

The non-return valve [16] can be opened and closed manually by rotating it from closed position where the valve body is in line with the shaft axis (as shown in FIG. 7) to the open position where the valve body has rotated around the central headed screw (as shown in FIGS. 5 & 6). In the closed position, the ball valve closes off hole [18] which connects to hole [24] and hole [26] which has an opening at the end of the shaft. A secondary opening is closed off permanently by the set screw [25] and is only present to aid manufacture of the interconnecting holes. The plastic valve body [21] is flexible enough to allow the ball [23] to be pushed away from hole [18] by pressurised air or water flowing through the hole. However when the air or water is not under pressure or if it's under low pressure, the ball valve [23] is biased closed sealing the hole [18]. Those familiar with the art of fluid control and/or pneumatics will appreciate that there are a number of different non-return valves designs and standard products. A number of different arrangements could be used to establish the non-return valve function required apart from the embodiment shown here, including use of a standard (off the shelf) non-return valve. A protruding feature [28] at the opposite end of the valve body falls into a recess [27] on the shaft [15] to retain the valve in the closed position, preventing accidental opening except when it is required to be manually opened. The flexible properties of the plastic valve body enables the protrusion [28] to climb out of the recess [27] when manually turned to the open position.

The in-use function will now be described with reference to FIGS. 9-20.

Figure 9:
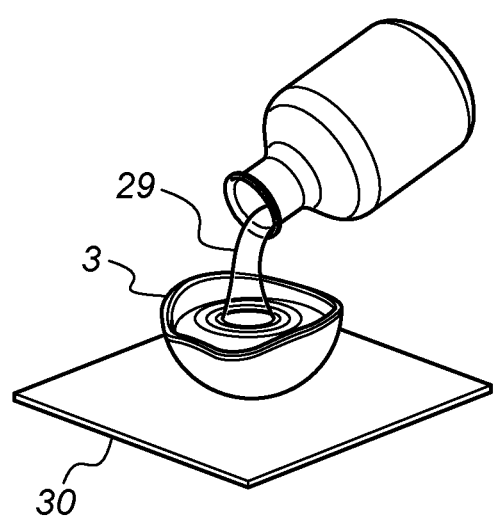

The cup implant [3] is removed from sterile packaging and placed on a flat surface [30]. It is then filled with sterile water [29] as shown in FIG. 9.

Figure 10:
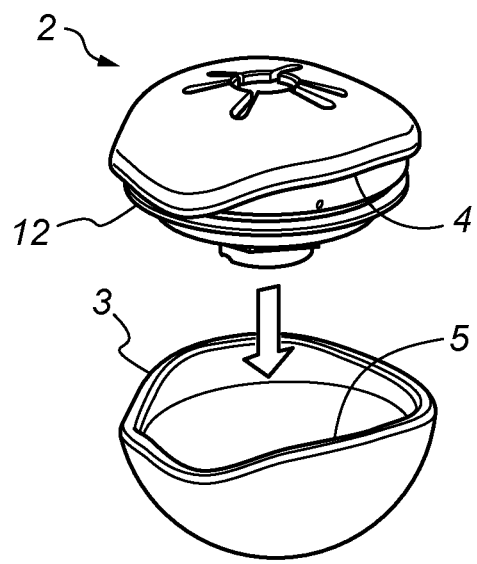

With the cup still on a flat surface to avoid spillage, the cover [2] is inserted into the cup [3] with contours [4&5] (if present) approximately aligned as shown in FIG. 10.

Figure 11:
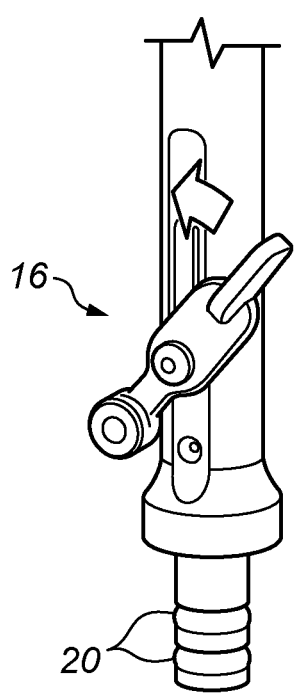

The introducer is prepared by manually closing the non-return valve in the direction of the arrow as shown in FIG. 11. The valve body [21] should be in line with introducer shaft [15].

Figure 12:
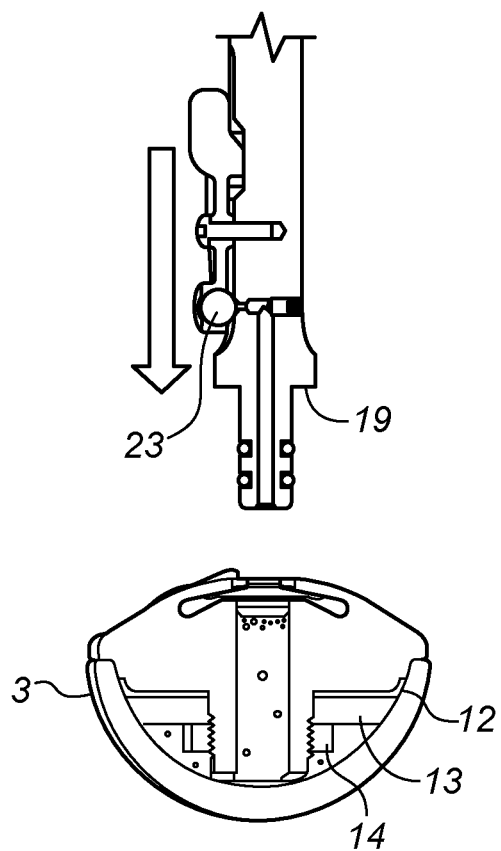
Figure 25:
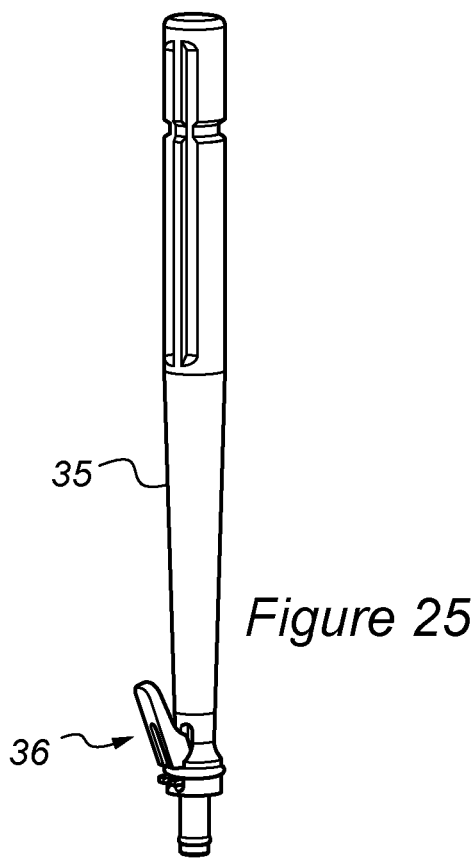
Figure 26:
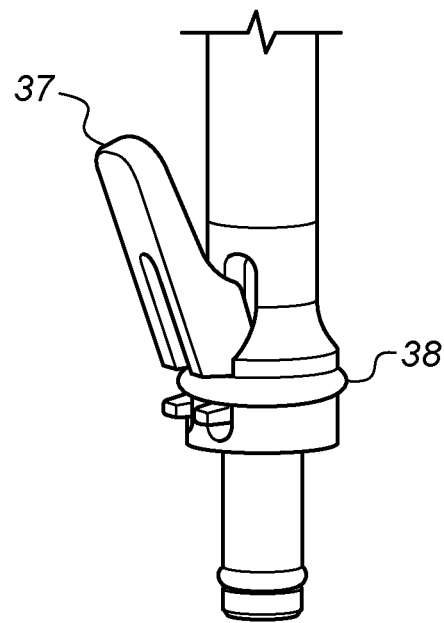

Next, with the cup and cover still on a flat surface to avoid spillage the introducer is inserted into the cover (introducer spigot [17] inserts into cover aperture [9]) as shown in FIGS. 12 & 13. FIG. 13 shows that once the seals (cover seal [12] with cup and introducer seals [20] with cover) are engaged, excess water from the sealed cavity is expelled via the non-return valve [16]. However water and air are prevented from returning to the cavity because the valve closes automatically as shown in FIG. 14. To emphasis this point, FIG. 15 is a close up view of FIG. 13 with the ball valve [23] opened by water escaping and FIG. 16 is a close up view of FIG. 14 with ball valve closed sealing the cavity.

For clarity, in FIG. 14, only enough force to insert the introducer has been employed, so the flange [19] of the introducer is resting on top of the light flexing fingers [6] on the cover without bending them. It is then easier to show the progression from FIG. 14 to FIG. 17 where the light flexing fingers [6] are bent down (stage 1) however in reality this is likely to happen simultaneously as the introducer is inserted. The light flexing fingers bending down this far reduces the volume of the enclosed cavity slightly and a little more water is expelled from the non-return valve as shown in the inset close-up of FIG. 17. Low pressure is maintained because the light flexing fingers [6] remain within elastic limits and are trying to return to their un-flexed state thereby holding the fluid at low pressure and keeping them in the bent down position. The low pressure state of the fluid pulls together all three elements with a holding force between them. This holding force is sufficient to manipulate the cup into position in the patient's hip socket.

FIG. 18 shows the progression from light flexing stage (stage 1) to stiffer flexing stage (stage 2) following impaction of the full assembled device by the surgeon to begin jam fitting the cup implant in the hip socket. These impaction forces are much greater and sufficient to bend down the stiffer flexing fingers [7] and light flexing fingers [6] to their fully bottomed out position. All the fingers bending down fully reduces the volume of the enclosed cavity slightly again and a little more water is expelled from the non-return valve [16] as shown in the inset close up of FIG. 17. Even lower pressure is maintained because the flexing fingers [6&7] are still within elastic limits and trying to return to their un-flexed state with considerable force, thereby holding the fluid at even lower pressure and keeping all the fingers in the fully bent down position as shown in FIG. 19. The low pressure state of the fluid pulls together all three elements with a greater holding force between them. It is desirable to have a stronger hold as the cup is impacted because it may veer out of alignment as the jam fit increases or the surgeon may wish to adjust alignment as the cup advances toward full seating. Furthermore it is desirable for the cover to regain the stiffness of a solid part (stage 2) so that the force of the hammer blows is transferred efficiently to where it is needed and the surgeon can maintain 'feel' and detect when the cup is fully seated.

Figure 29:
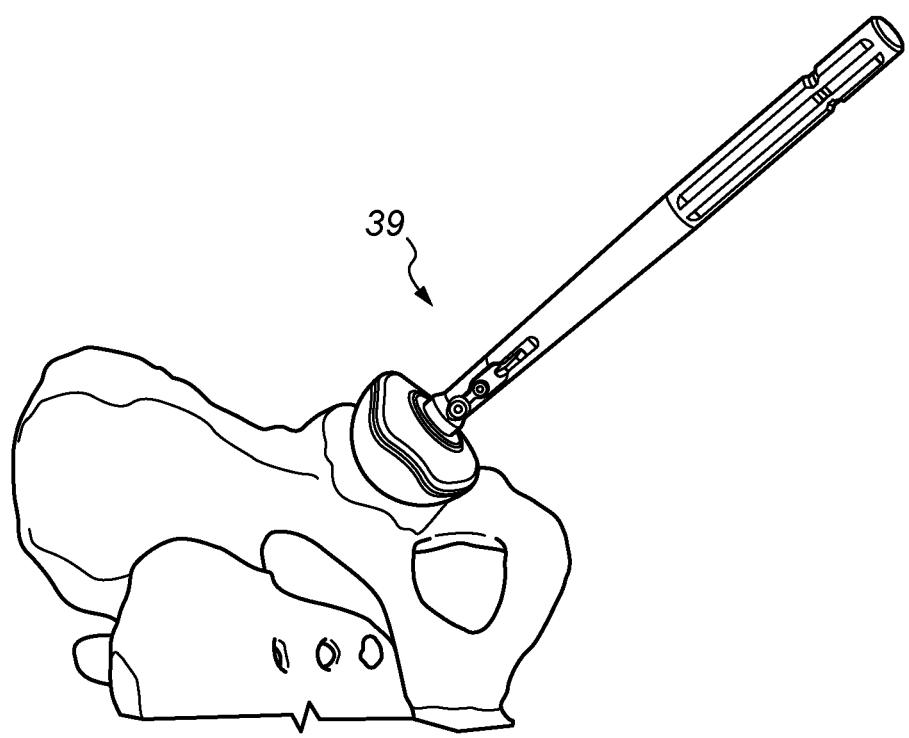

FIG. 29 shows the assembled device [39] as the cup implant is inserted into a patient's hip socket, however the hammer used by the surgeon impact the shaft and jam fit the cup implant is not shown.

FIG. 20 shows that the holding grip is released by manually opening the non-return valve [16], uncovering the small hole [18] in the shaft and allowing air in to normalise the low pressure and break the seals. The cover will come away with the introducer due to the friction fit between the O-rings on the shaft spigot [20] and the aperture [9] on the cover.

An alternative embodiment of the cover [31] is shown in FIGS. 21-24. In this arrangement, the seal between cover [31] and cup implant is made by a large O-ring [32] which is housed in a groove [32] on the cover [31]. Preferable the O-ring groove will follow the contour but alternatively it could be circular without undulations. In this embodiment the cover consists of only 2 parts, the cover body [31] and O-ring [32]. This embodiment has a slightly different array of light flexing fingers [33] and stiffer flexing fingers [34]. The function is the same as described above. Preferably the body is manufactured in plastic (such as nylon) which will not damage the implant bearing surfaces. The O-ring is manufactured from a soft material such as silicone, which conforms to make a seal with cup bearing surface. Alternatively it could be manufactured in other soft materials such as nitrile rubber, thermoplastic elastomer (TPE), or polyurethane.

Figure 27:
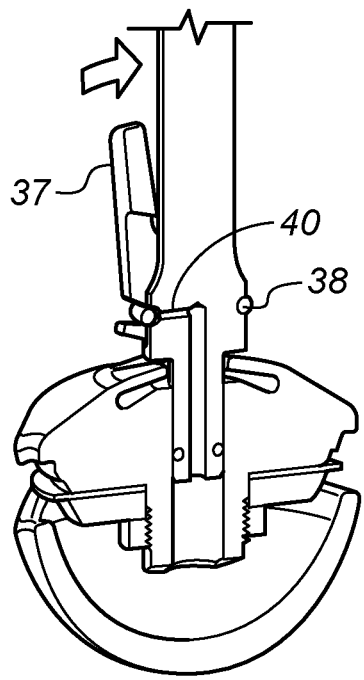
Figure 28:
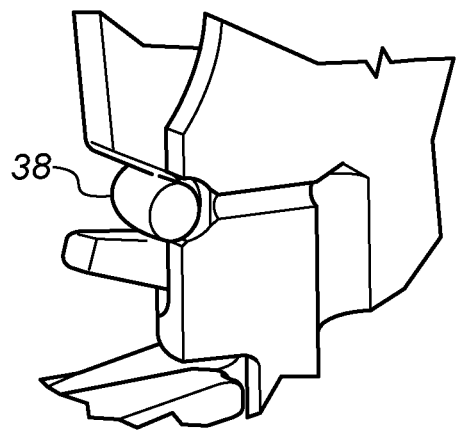

An alternative embodiment of the introducer is shown in FIGS. 25-28. In this arrangement, the non-return valve [36] is formed by an O-ring [38] covering the small hole. The O-ring is under slight tension, so that it seals the hole, except when pushed away by pressurised air or water flowing through the hole [40]. However when the air or water is not under pressure or if it's under low pressure, the O-ring [38] seals the hole [40]. Manual opening of this version of the non-return valve is achieved by pressing the lever [37] which is captivated by the O-ring [38]. When pressed, the lever rocks on a fulcrum and prises the O-ring away from the hole [40] as shown in FIGS. 27 & 28.

Figure 30:
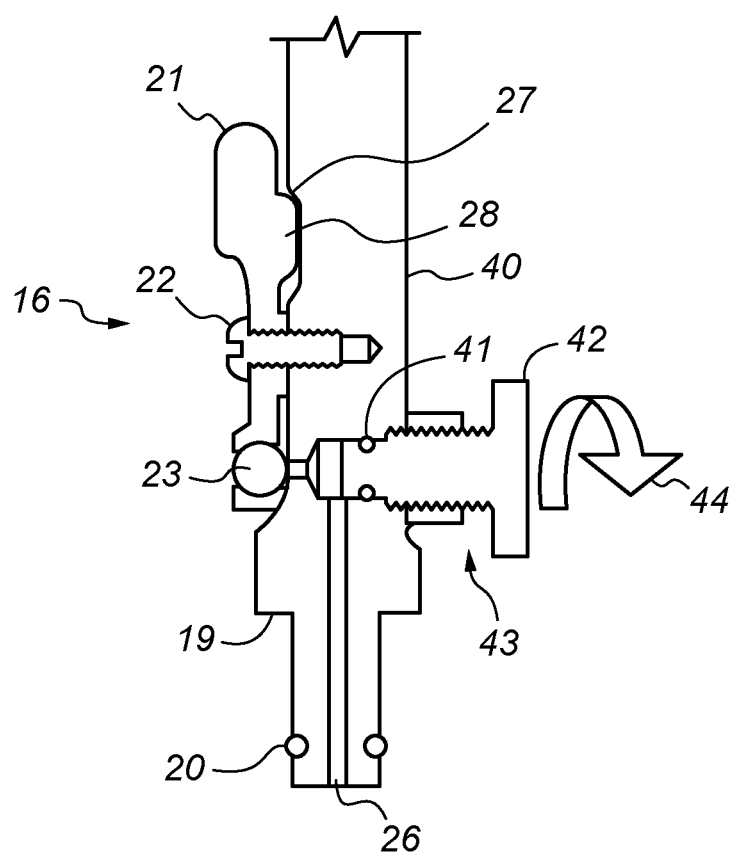

Another alternative embodiment of the introducer is shown in FIG. 30. It includes the same non return valve [16] which can be manually released as seen in earlier embodiments. However there is included a screw plunger [43] who's role is to further reduce fluid pressure in the sealed cavity. The screw plunger consists of screw [42] with O-ring seal [41]. The screw has a male screw thread which engages with mating female screw thread on the introducer body [40]. When assembled with the cup implant and cover, as the screw is turned in direction of arrow [44], the plunger is drawn back and because a seal is made between plunger and hole, this acts to further reduce fluid pressure and enhance the holding grip between cup implant, cover and introducer. This additional screw plunger can either work in parallel with the resilient feature on the cover, or it can be an alternative to it.

Figure 31:
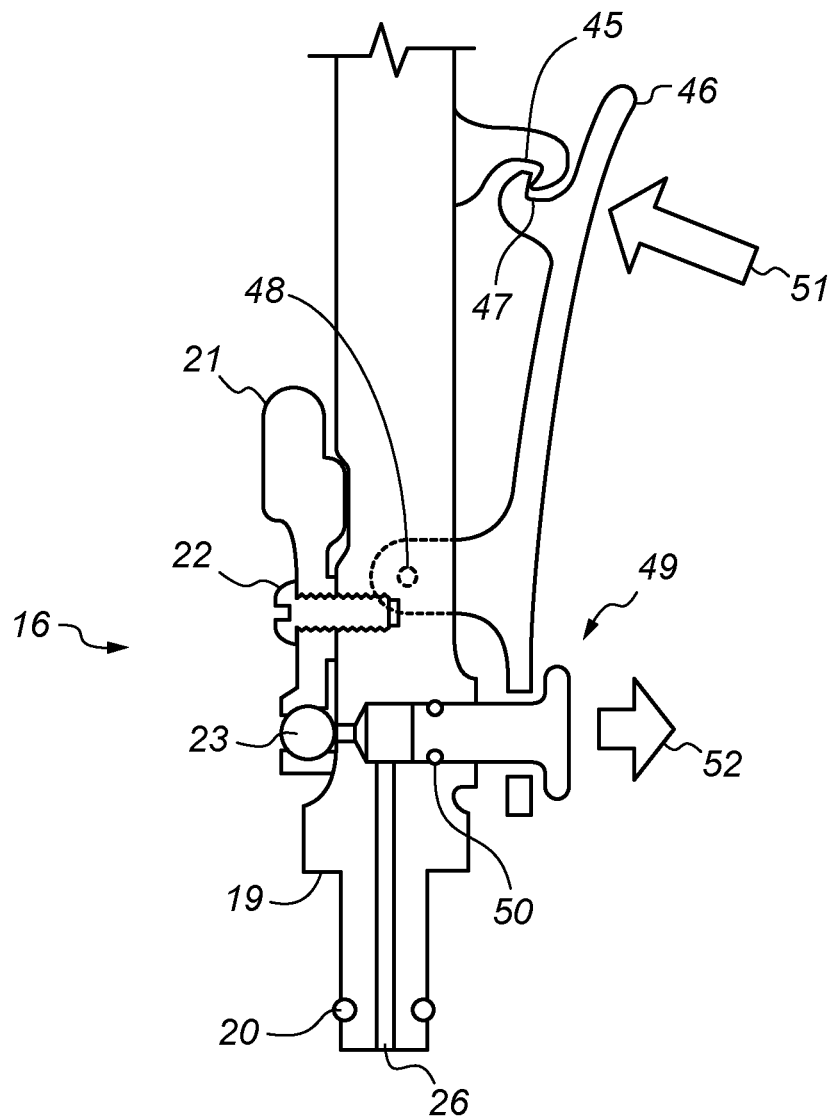

Another alternative embodiment of the introducer is shown in FIG. 31. It includes the same non return valve [16] which can be manually released as seen in earlier embodiments. However similar to the embodiment in FIG. 30, there is included a plunger [49] who's role is also to further reduce fluid pressure in the sealed cavity. In this embodiment the plunger is drawn out by a lever [46] which toggles about pivot pin [48] and is held in the drawn out position by latch feature [47] which engages with corresponding latch [45] on the main body of the introducer. The lever 46 has resilient leaf spring qualities so that it bends to latch and therefore continues to bias the plunger into a further drawn out position when latched. This additional levered plunger can either work in parallel with the resilient feature on the cover, or it can be an alternative to it.

Figure 32:
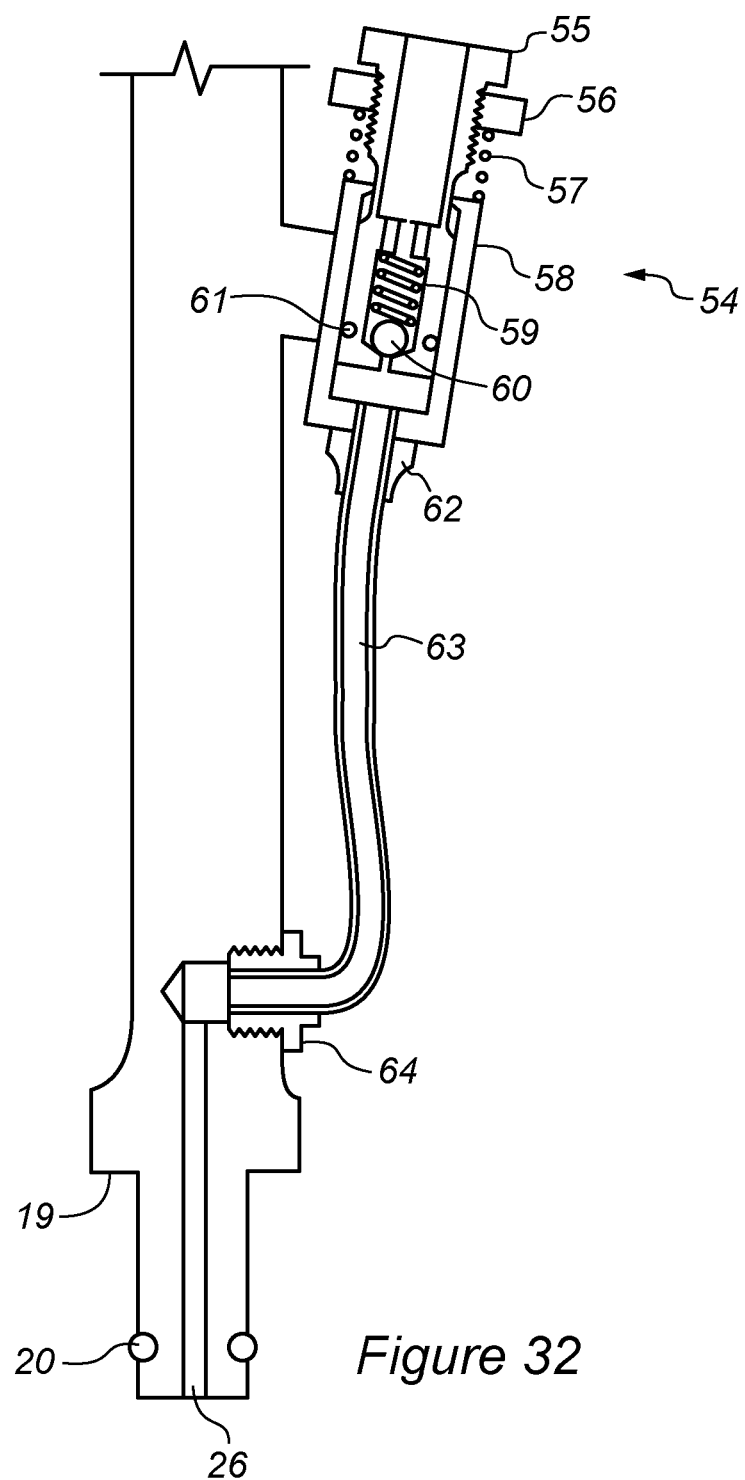

Another alternative embodiment of the introducer is shown in FIG. 32. In this embodiment, a self-contained plunger assembly is attached distally to the introducer shaft and is connected to the sealed cavity between cup implant, cover and introducer by a rigid tube [63]. The rigid tube includes screw connectors [62 & 64] to connect it to the plunger assembly and introducer body respectively. The plunger assembly consists of body [58], plunger [55], O-ring seal [61], ball-valve [60], light spring [59], screw collar [56] and strong spring [57]. The role of the plunger is to further reduce fluid pressure in the sealed cavity. The plunger assembly is activated by tightening screw collar [56] which compresses strong spring [57] and biases the plunger [55] to the drawn out position. This additional plunger assembly can either work in parallel with the resilient feature on the cover, or it can be an alternative to it.

Figure 33:
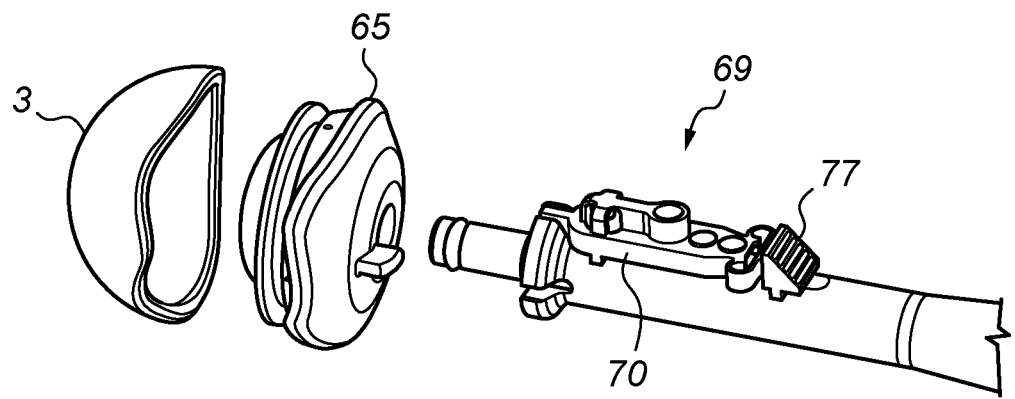
Figure 34:
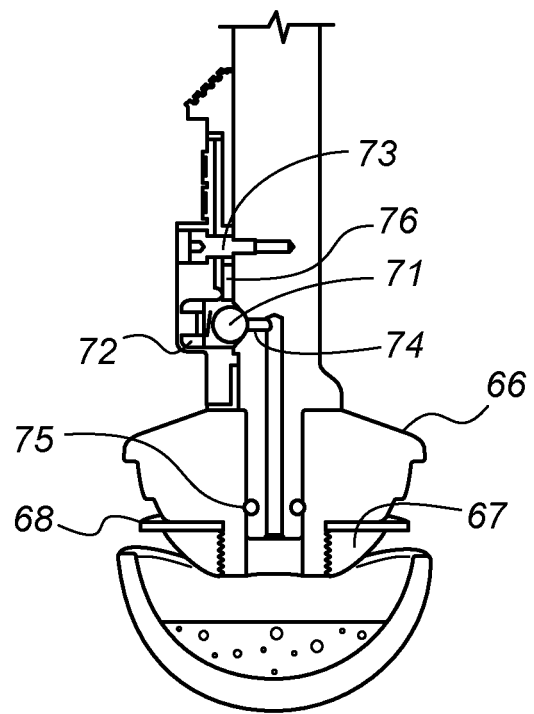
FIG. 34 is a cross sectioned view of the three elements (including liquid in the cup implant).
Figure 35:
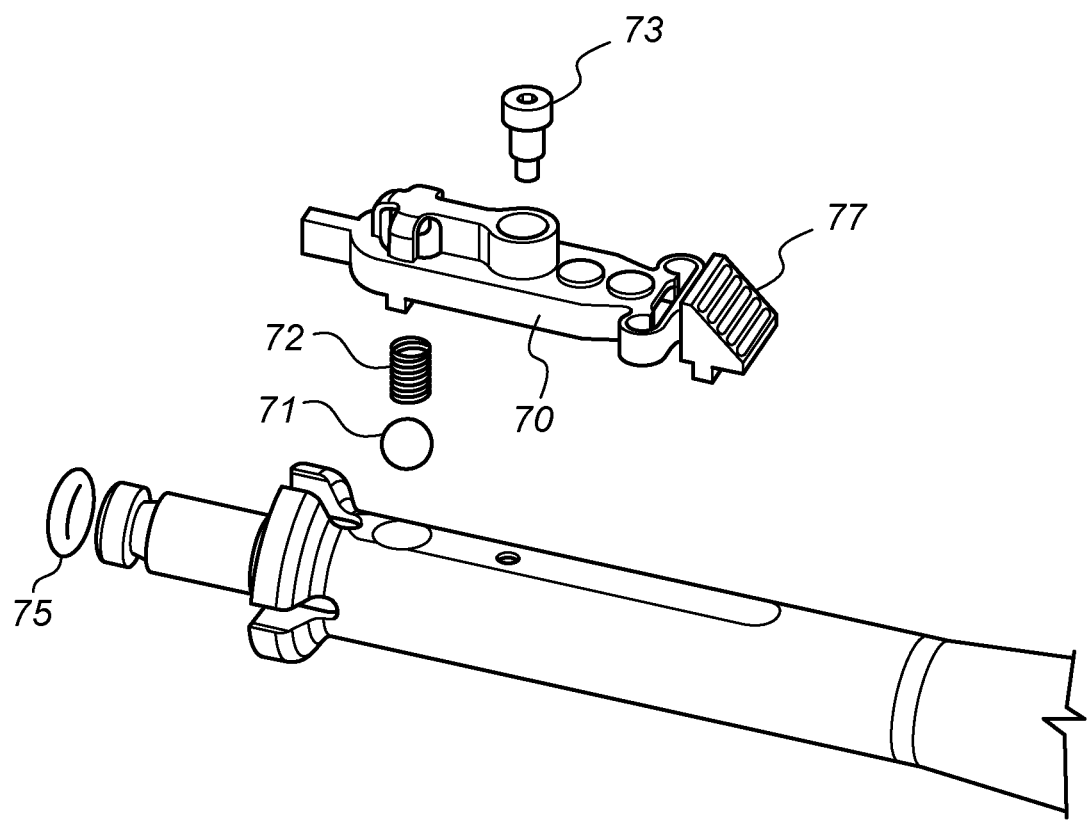
FIG. 35 is an exploded view of the introducer component parts.
Figure 36:
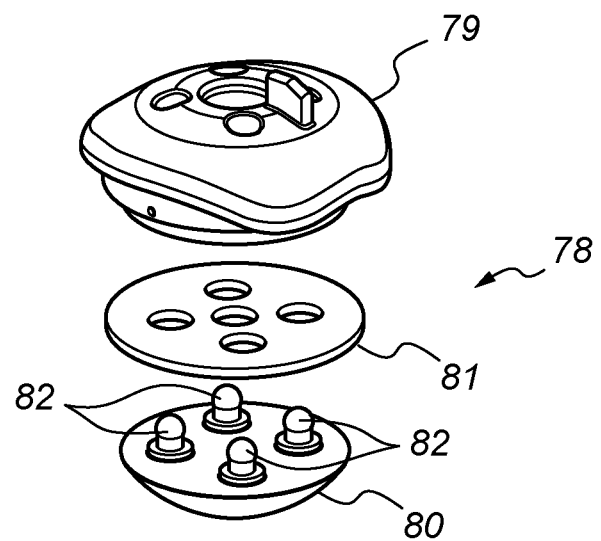
FIGS. 36-44 show a further alternative embodiment of the cover and introducer.
Figure 37:
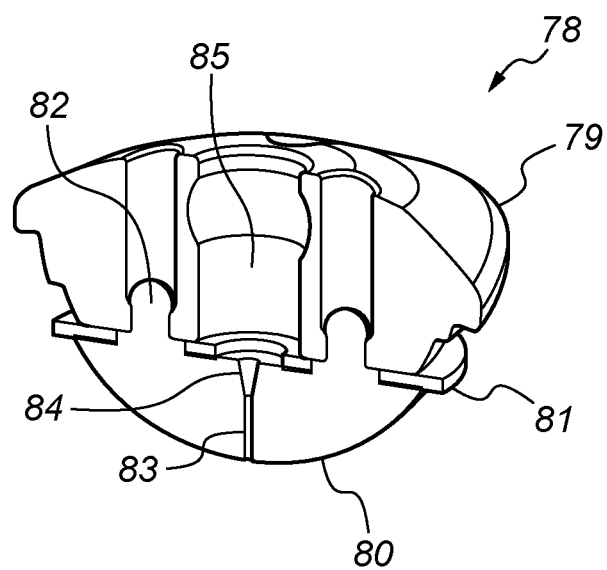

An alternative arrangement is shown in FIGS. 33-35. In this arrangement, the alternative cover [65] shown in FIGS. 33 and 32 comprises three parts, body [66], collar [67] and seal [68]. Preferably the cover is single use. When assembled together, the seal is sandwiched tightly between the body [66] and collar [67] which are either pressed together via an interference fit or screwed together via a screw thread. The body and collar are preferably manufactured in plastic (such as nylon), preferably by selective laser sintering (SLS) but alternatively by injection moulding. In this arrangement, the resilient deformable features of the cover as described above are not present. The seal [68] can be a flat circular disc with central hole and can be manufactured from a soft material such as silicone which flexes to conform to the cup implant bearing surface to make a watertight/airtight seal. Alternatively, the seal could be manufacture in nitrile rubber, thermoplastic elastomer (TPE), or polyurethane. Preferably the seal is die cut from sheet material.

Also in FIGS. 33, 34 and 35, the component parts of the non-return valve assembly [69] can be identified. Valve body [70], valve ball [71], compression spring [72] and exemplary optional fixing means (e.g. headed screw) [73]. Under pressure of the compression spring, the valve ball closes off hole [74] in the introducer, which in combination with the other two seals, 68 and O-ring [75], encloses the sealed cavity of liquid which has been previously described. Although a compression spring is described, it will be appreciated that alternative biasing means can be used which are well known in the art. In this arrangement, the valve is opened by a sliding portion [76] of the valve body [70] operated by pressing button [77]. This sliding portion presses against the valve ball [71], displacing it sideways to temporarily open hole [74] in the introducer. When the button is released, the valve automatically closes once again. The function of this alternative embodiment is as previously described, except that the hold between the three elements relies jointly upon to the adhesive/cohesive forces in the liquid and the seals preventing air from entering the cavity. It is not embellished by a reduction in pressure brought about by the resilient deformable features of the cover shown in FIGS. 1-4, 10-14, 17-24 and 27, in this case not present.

An alternative arrangement is shown in FIGS. 36-44. In this arrangement, the alternative cover [78] shown in FIGS. 36 & 37 comprise three parts, body [79], collar [80] and seal [81]. Preferably the cover is single use. When assembled together, the seal is sandwiched tightly between the body [79] and collar [80] which optionally is pressed together via several snap fit pegs [82] preferably four snap fit pegs. The collar [80] preferably has a small through hole [83] ending in a conical shape [84] adjacent to the larger central hole [85] in the cover body [79]. The body and collar are preferably manufactured in plastic (such as nylon), preferably by selective laser sintering (SLS) but alternatively by injection moulding. In this arrangement, as with the arrangement in FIGS. 33-35, the resilient deformable features of the cover are not present. The seal [81] can be a flat circular disc with an array of holes corresponding to the snap fit pegs [82] and can be manufactured from a soft material such as silicone which flexes to conform to the cup implant bearing surface to make a watertight/airtight seal. Alternatively, the seal could be manufactured in nitrile rubber, thermoplastic elastomer (TPE), or polyurethane. Preferably the seal is die cut from sheet material.

Figure 38:
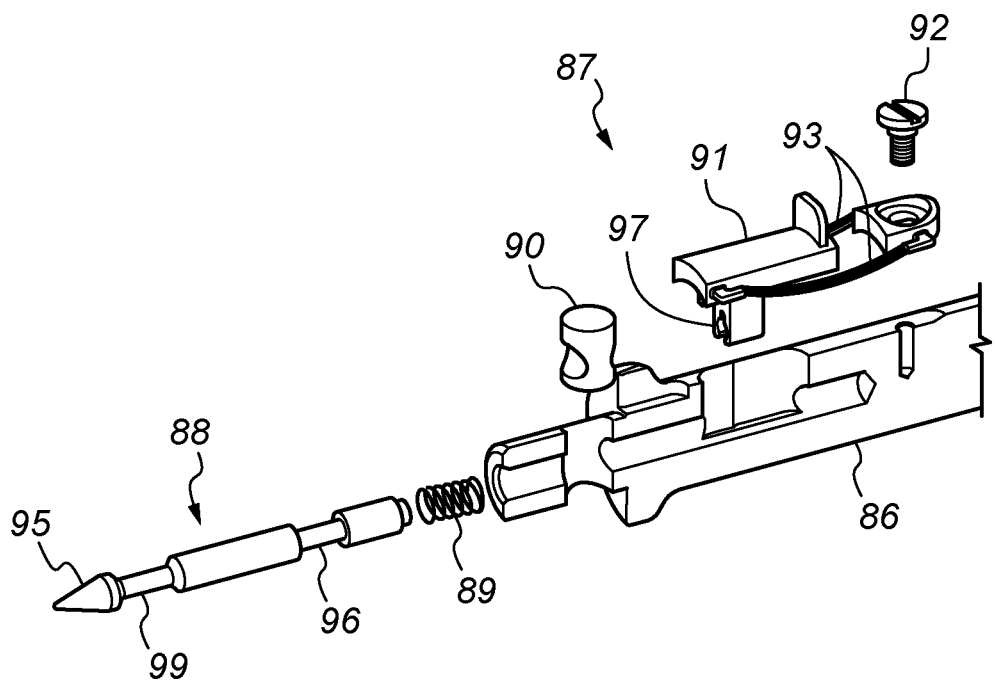
Figure 39:
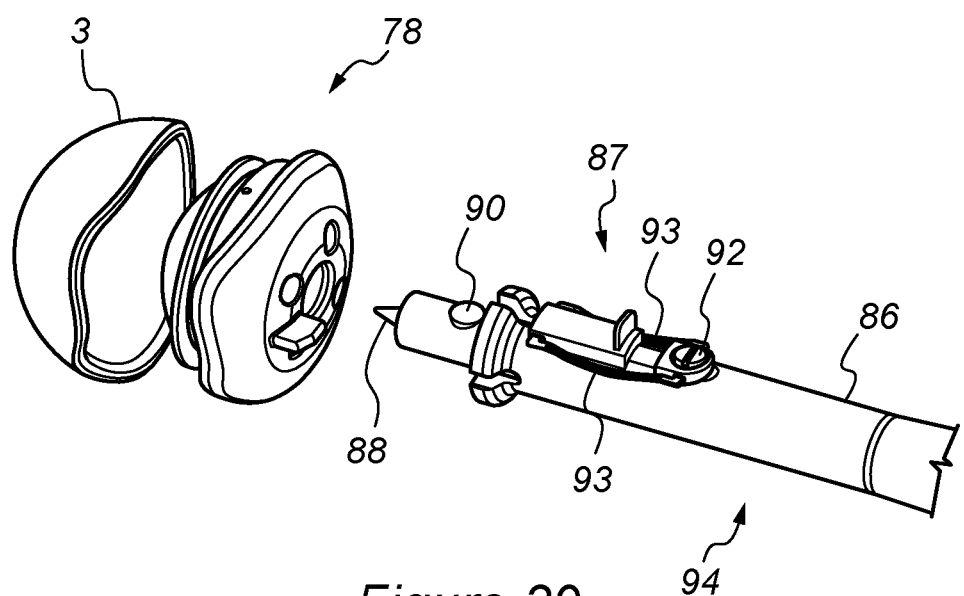
Figure 40:
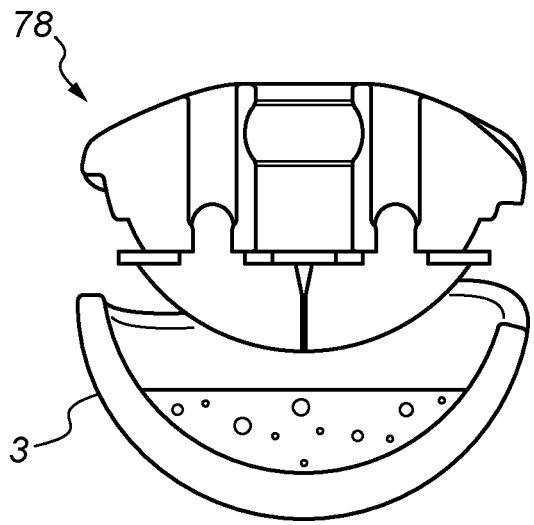

In FIGS. 38 and 39, the introducer body [86] is shown and the component parts of the non-return valve assembly [87] can be identified; Valve pin [88], compression spring [89], locking button [90], release slider [91] and exemplary optional fixing means (e.g. headed screw) [92]. The valve pin can be made of any suitable material—it is preferably manufactured in stainless steel, optionally with a very good machined finish or polished finish. The finish is preferably one which provides a smooth surface which permits suitable sealing of the pin on/in the channel. The release slider [91] and locking button [90] are preferably manufactured in plastic (such as nylon), preferably by selective laser sintering (SLS) but alternatively by injection moulding. The release slider optionally incorporates integral leaf springs [93] to bias it to the forward (valve closed) position.

Figure 42:
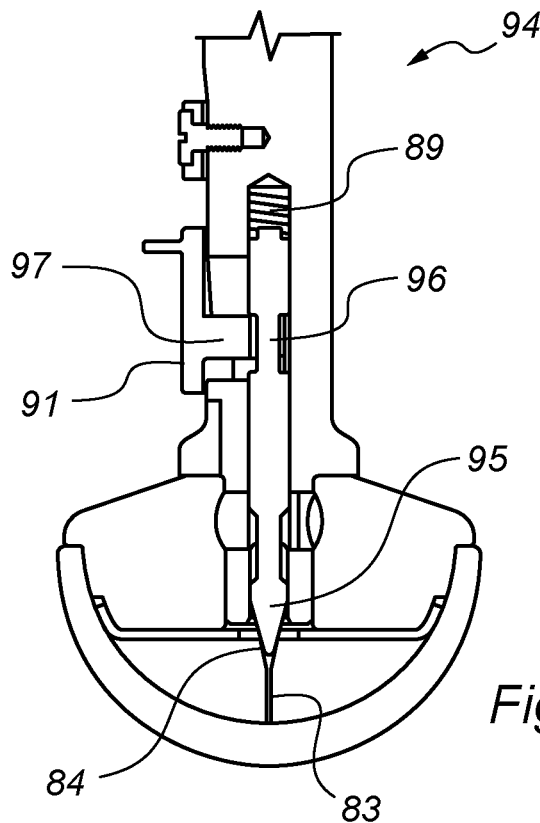

In FIG. 42 it can be seen that the pointed end [95] of valve pin [88] blocks the conical opening [84] to hole [83] in collar [80] under pressure from spring [89]. Although a spring is described, it will be appreciated that alternative biasing means can be used which are well known in the art. This provides the non-return valve function. Further it can be seen that the yoke portion [97] of release slider [91] engages with a groove [96] on valve pin [88] and acts to move the valve pin (releasing the non-return valve) against pressure from spring [89].

Although the end of the valve pin has been described as "pointed", and the opening [84] has been described as "conical", it will be appreciated that the concept behind the pin and the opening is that the pin is able to block the opening to provide a suitable sealing force between the two such that the ingress of fluid is substantially prevented. In this regard, therefore, the exact geometry of the profiles of the pin and the opening are not important. What is more important is that the profiles are complementary in order to effect suitable sealing. In this regard, therefore, the profiles could be e.g. convex/concave (respectively), or other complementary arrangements.

The in-use function will now be described with reference to FIGS. 40-44.

Figure 41:
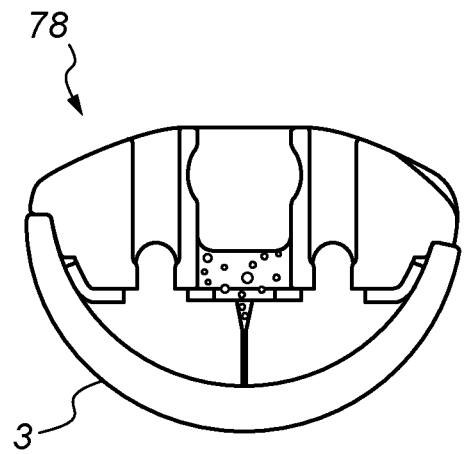

The cup implant [3] is removed from sterile packaging and placed on a flat surface. It is then filled with sterile water as described previously. The cover [78] is inserted into the cup implant [3] as shown in FIG. 41. The introducer [94] is then inserted into the cover as shown in FIG. 42. Air and excess water is expelled via the non-return valve [87], however water and air are prevented from returning to the cavity because the valve closes automatically under pressure from the compression spring [89]. A hold is established between the cup implant and cover due, jointly, to the adhesive/cohesive forces in the liquid and the seal and valve preventing air from entering the cavity of fluid. Furthermore, in some preferred arrangements a mechanical lock is established between the introducer and cover via a locking means e.g. the locking button [90]. With all three elements held together, the cup implant can be positioned and forcibly fitted into a pre-prepared hip socket (as shown previously in FIG. 29).

Figure 43:
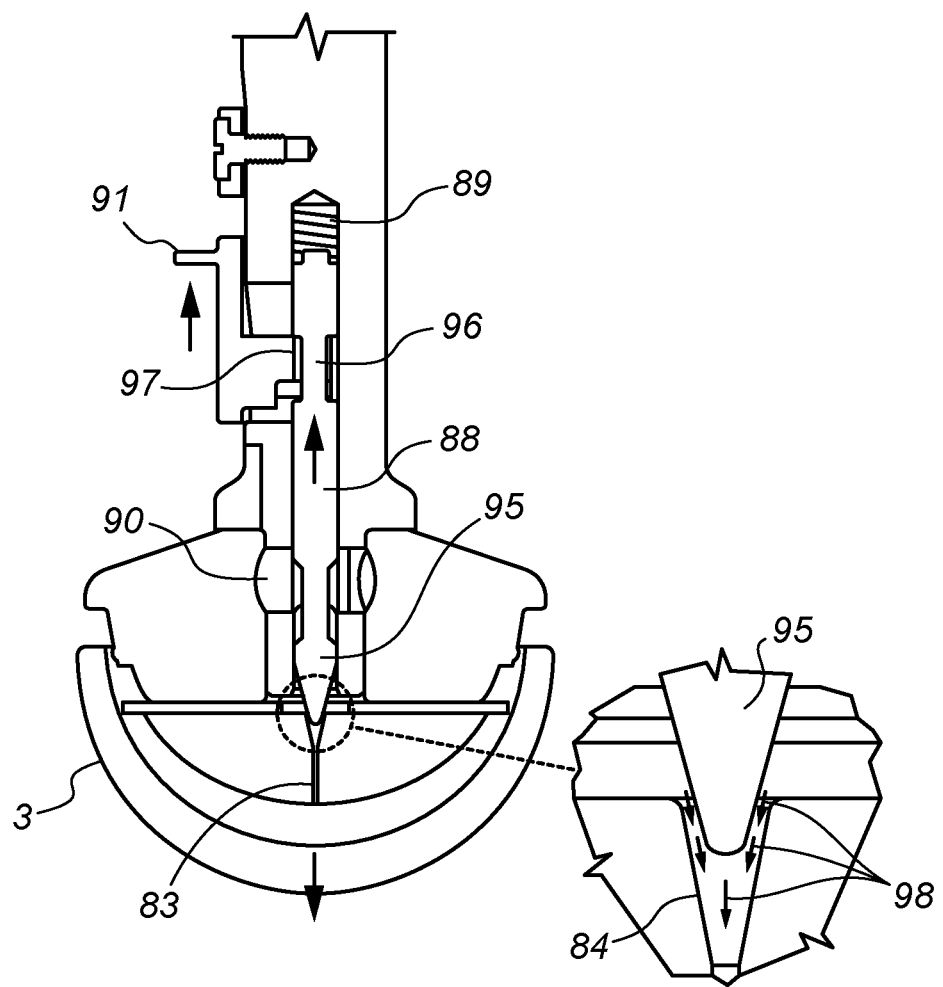
Figure 44:
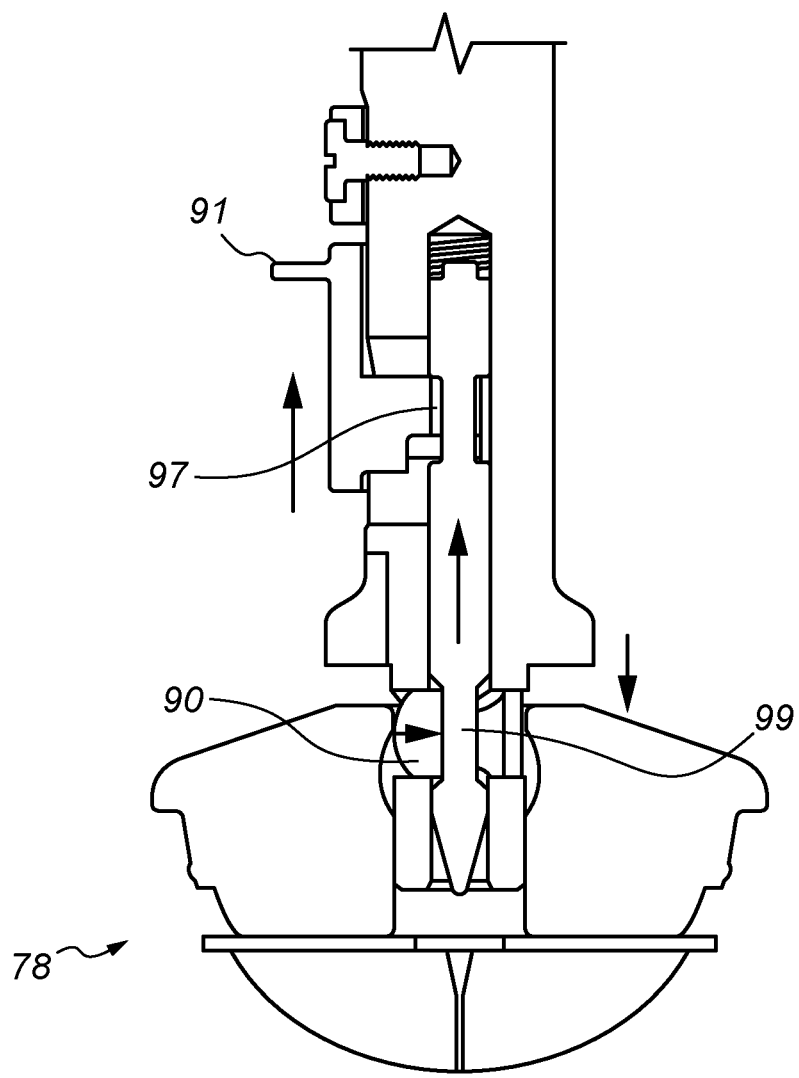

In FIG. 43, it can be seen that the first small movement of the release slider lifts the valve pin [88], pulling the pointed end [95] from the valve seating [84] on the cover to open the valve. Once the valve is opened, air can enter the cavity as shown by the small arrows [98] in FIG. 43, which acts to release the hold between the cup implant and the cover. At this stage, where the introducer comprises a locking mechanism, the cover is still locked to the introducer by the locking button [90]. However as shown in FIG. 44, further upward movement of the release slider [91] also releases the cover from the introducer because groove [99] on the valve pin [88] is moved in line with the locking button [90] allowing it to shift sideways and release the cover [78] from the introducer.

The cover assembly may further comprise an undercut region in the channel extending from the distal end to the proximal end, with the undercut region being located towards the proximal end of the cover assembly. The locking mechanism and the undercut region preferably comprise a complementary profile. The undercut region preferably has smoothed sides to prevent snagging of the locking mechanism and to assist the locking button to engage and disengage smoothly.

It will be appreciated that there is also provided a method comprising the use of the systems as described herein.

Furthermore, any of the discussion of the various components of the systems (or the systems themselves) with particular regard to specific arrangements is also intended to be equally applicable to those components when used in the alternative arrangements discussed herein. Thus, when detailed discussion of particular components follows a more general discussion of an arrangement of the system, it is intended that the detailed discussion of the particular components is also applicable to alternative arrangements, even if not discussed in detail in relation to those arrangements.

It is to be understood that it is common practice in the field of cup implants to use an insert with the cup implant in order e.g. to improve grip on the implant (the insert is typically arranged to be fixed to complementary features on the inner surface of the implant) or to provide protection to reduce potential damage to one or more surfaces of the implant. Thus, the person of skill in the art will appreciate that reference to an implant as discussed herein can optionally include reference to an insert that is attached to the implant.

Some preferred embodiments of the present invention are described below from E1 to E40.

E1. A system comprising a medical instrument and a holding device that interacts with said medical instrument, wherein the interaction between the medical instrument and the holding device creates a cavity between said medical instrument and said holding device, said holding device comprising means to allow the cavity to be sealed, said system comprising:
　a) means to create a low pressure or suction within the cavity;
　b) means to maintain said low pressure or suction.

E2. A system according to E1, said system further comprising:
　c) means to reduce cavity volume from its initial volume, said initial volume being the volume of said cavity when the holding device is inserted into said medical instrument to a predetermined position;
　d) means to maintain said reduced cavity volume.

E3. A system according to E1 or E2, said system further comprising a fluid, said fluid being introduced to said system such that said fluid is present in said sealed cavity, preferably where said fluid is liquid and where there is no or substantially no gas present in said sealed cavity.

E4. A system according to any preceding embodiment, said system further comprising means to release fluid low pressure or suction.

E5. A system according to any preceding embodiment, said system further comprising:
　means to introduce fluid to said cavity; and/or
　means to expel surplus gas and/or liquid.

E6. A system according to any preceding embodiment, wherein the holding device comprises a cover assembly for placing into said medical instrument, said cover assembly comprising:
　a proximal surface, said proximal surface comprising a region that is able to interact with an impaction device;
　a distal surface located away from the proximal surface of the cover assembly and arranged to fit in said medical instrument, said distal surface comprising at least a seal.

E7. A system according to E6, wherein said cover assembly further comprises:
　at least one resilient and elastically deformable region associated with the cover assembly such that when elastically deformed in a stressed state there is natural bias of the resilient and elastically deformable region to revert to its unstressed state.

E8. A system according to E7, wherein the resilient and elastically deformable region is, or is associated with, a portion of the proximal surface of the cover assembly.

E9. A system according to E7 or E8, wherein the resilient and elastically deformable region is, or is associated with, a portion of the distal surface of the cover assembly.

E10. A system according to any of E7-9, wherein the resilient and elastically deformable region is formed integrally with the cover assembly.

E11. A system according to any of E7-10, wherein the resilient and elastically deformable region is formed from a portion of material extending from the cover assembly.

E12. A system according to E11, wherein said portion of material extending from the cover assembly comprises a different material from the respective surface of the cover assembly.

E13. A system according to E11, wherein the portion of material is an extension of the material forming the respective surface of the cover assembly.

E14. A system according to any of E11-13, wherein the portion of material extending from the cover assembly comprises at least one fin.

E15. A system according to E14, wherein the at least one fin comprises a plurality of fins, one or more of said plurality of fins being of substantially the same dimensions.

E16. A system according to E14 or E15, wherein the at least one fin comprises a plurality of fins, one or more of said plurality of fins being of differing dimensions.

E17. A system according to any of E7-16, wherein the resilient and elastically deformable region comprises one or more springs, one or more washers (e.g. Belleville washers), or a combination of springs and washers.

E18. A system according to any of E7-17, wherein the cover assembly is structured such that at least a portion of the resilient and elastically deformable region is able to reach a stop when under stress and prior to loss of elastic deformation, the stop forming a platform whereby the resilient and elastically deformable region effectively forms a non-moving unit with the main body of the cover assembly such that force is able to be transmitted efficiently throughout the resilient and elastically deformable region and main body of the cover assembly.

E19. A system according to E18, wherein the stop forming the platform which the resilient and elastically deformable region contacts when under stress is suitably spaced from resilient and elastically deformable region, such that the portion of the resilient and elastically deformable region that comes into contact with the platform does so prior to any plastic deformation resulting in loss of bias to the unstressed state.

E20. A system according to any of E6-19, wherein said cover assembly comprises a hole extending from and through the proximal surface to and through the distal surface.

E21. A system according to any of E6-20, wherein said cover assembly further comprises a hole in the distal surface beyond the seal, said hole extending into the cover assembly but not penetrating through the proximal surface.

E22. A system according to any of E6-21, wherein said cover assembly comprises multiple parts which fit together to form the cover assembly, said multiple parts comprising:
　a first part comprising at least said proximal surface, optionally also comprising said distal surface; optionally a second part comprising said distal surface;

a seal; and means for securing said seal to said first and/or second part.

E23. A system according to any preceding embodiment, further comprising an impaction device, said impaction device comprising a part that interacts with at least a part of said cover assembly.

E24. A system according to E23, wherein said impaction device comprises:
 a proximal end;
 a shaft; and
 a distal region containing a channel, said channel comprising an entry port at the distal end/tip of said distal region and an exit port at a point on the shaft away from the distal end/tip, said impaction device further comprising means to removably block the exit port.

E25. A system according to E24, wherein the means to removably block the exit port is a non-return valve.

E26. A system according to E25, wherein said non return valve is a ball valve and/or an o-ring or the like.

E27. A system according to any of E23-26, wherein said holding device comprises a cover assembly comprising a hole extending from and through a proximal surface to and through a distal surface of the cover assembly, at least a portion of said hole dimensioned to receive a portion of said impaction device.

E28. A system according to any of E23-27, wherein the impaction device comprises a flange in the distal region, said flange being able to interact with the holding device to stabilise the siting of the impaction device on or in the holding device.

E29. A system according to any of E24-28, wherein the impaction device further comprises a mechanism to create a low pressure or suction within the cavity, such as by use of a plunger in communication with said channel, said plunger being adjustable to draw or push the fluid within the channel and hence in said cavity.

E30. A system according to any of E23-29 as dependent on any of E7-19, wherein suitable pressure exerted on the impaction device permits the elastic deformation of at least a portion of the resilient and elastically deformable region towards the distal surface of the cover assembly.

E31. A system according to E30, wherein the cover assembly is structured such that at least a portion of the resilient and elastically deformable region is able to reach a stop when under stress, the stop forming a platform whereby the resilient and elastically deformable region effectively forms a non-moving unit with the main body of the cover assembly such that force is able to be transmitted efficiently throughout the resilient and elastically deformable region and main body of the cover assembly and wherein further elastic deformation of the portion of the resilient and elastically deformable region is prevented by the stop.

E32. A method of holding a medical implant using a fluid, preferably a liquid, the fluid being introduced to the medical implant and the medical implant thereafter being capped with a holding device, the holding device comprising a cover assembly arranged to displace excess fluid from the cavity formed between the medical implant and the cover assembly and to form a seal, the holding device thereafter being manipulated in order to create a suction force within the cavity and to maintain said suction.

E33. A method according to E32, wherein said manipulation further comprises reducing the cavity volume from its initial volume, said initial volume being the volume of said cavity when the holding device is inserted into said medical instrument to a predetermined position, and maintaining said reduced cavity volume.

E34. A method according to E32 or E33, wherein the holding device comprises a cover assembly comprising a resilient and elastically deformable region, said manipulation of said cover assembly acting on at least a portion of said resilient and elastically deformable region to reduce the volume of the cavity, the resilient and elastically deformable region thereafter being prevented from returning to a relaxed state resulting in the reduction of pressure of fluid within the cavity.

E35. A method according to any of E32-34, said method comprising the steps of:
 (a) introducing fluid, preferably a liquid, to a cavity of said medical implant;
 (b) introducing said cover assembly of said holding device into said cavity of said medical implant, said cover assembly displacing excess fluid present in said cavity and forming a first seal between said cover assembly and said medical implant.

E36. A method according to E35, further comprising the steps of:
 (c) introducing an impaction device to said cover assembly;
 (d) further fluid from said cavity being removed.

E37. A method according to E34, further comprising the steps of applying pressure to said impaction device to elastically deform at least a portion of the resilient and elastically deformable region of said cover assembly, the deformation resulting in a further reduction in the available cavity space of the medical implant and the displacement of further fluid from said cavity.

E38. The method of E37, further comprising the step of:
 (e) applying further pressure to said impaction device such that said resilient and elastically deformable region contacts a stop on the cover assembly, said stop forming a platform that prevents the resilient and elastically deformable region from plastic deformation resulting in loss of bias to the unstressed state, and furthermore allows force is able to be transmitted efficiently throughout the resilient and elastically deformable region and main body of the cover assembly.

E39. A method according to any of E32-38, wherein the method comprises use of the system of any of E1-31.

E40. A method according to any of E32-39, said method further comprising the step of creating a breach in the seal between the medical implant and the holding device in order to release the holding device from the medical implant.

E41. A system comprising:
 (i) a medical instrument and a holding device that interacts with said medical instrument or that interacts with an insert positioned in/on said medical instrument, wherein the interaction between the medical instrument and/or insert and the holding device creates a cavity between said medical instrument and/or insert and said holding device, said holding device comprising means to allow the cavity to be sealed, wherein the holding device comprises a cover assembly for placing into said medical instrument and/or insert, said cover assembly comprising:
  a proximal surface, said proximal surface comprising a region that is able to interact with or receive an impaction device;
  a distal surface located away from the proximal surface of the cover assembly and arranged to fit in said medical instrument and/or insert, said distal surface comprising at least a seal;
  and (ii) an impaction device, said impaction device comprising:
- a proximal end;
- a shaft; and
- a distal region that interacts with at least a part of said cover assembly, said distal region containing a channel, said channel comprising an entry port at the distal part of said distal region and an exit port at a point on the shaft away from the distal part, said impaction device further comprising means to removably block the exit port;

wherein the arrangement of said medical instrument and/or insert, said holding device, and said impaction device forms:
- a) a means to create a low pressure or suction within the cavity; and/or
- b) a means to maintain said low pressure or suction.

The invention claimed is:

1. A system comprising:
a medical instrument and a holding device that interacts with said medical instrument or that interacts with an insert positioned in/on said medical instrument, wherein an interaction between the medical instrument and/or insert and the holding device creates a cavity within a resulting combination of said medical instrument and/or insert and said holding device which cavity is at least partially filled with fluid, wherein the holding device comprises a cover assembly for placing into said medical instrument and/or insert, said cover assembly comprising:
a proximal surface, said proximal surface comprising a region that is able to interact with or receive an impaction device;
a distal surface located away from the proximal surface of the cover assembly and arranged to fit in said medical instrument and/or insert, said distal surface comprising at least a seal; and
an impaction device, said impaction device comprising:
a proximal end;
a shaft; and
a distal region that interacts with at least a part of said cover assembly,
said shaft and/or distal region of said impaction device further comprising a mechanism that prevents additional fluid from entering the cavity.

2. A system as claimed in claim 1, wherein said cover assembly comprises a hole extending from and through a proximal surface to and through a distal surface of the cover assembly, at least a portion of said hole dimensioned to receive a portion of said impaction device.

3. A system as claimed in claim 2, wherein said distal region of said impaction device contains a channel, said channel comprising an entry port at a distal part of said distal region and an exit port at a point on the shaft away from the distal part, said impaction device further comprising means to removably block the exit port.

4. A system as claimed in claim 3, wherein the means to removably block the exit port is a non-return valve.

5. A system as claimed in claim 4, wherein said non return valve is a ball valve and/or an o-ring.

6. A system as claimed in claim 2, wherein said distal region of said impaction device comprises a pin, said pin being operable to releasably seal said cavity.

7. A system a claimed in claim 6, wherein a portion of the pin is profiled to fit into a complementarily profiled portion of the hole extending through the cover assembly.

8. A system as claimed in claim 1, wherein said distal region of said impaction device further comprises a locking mechanism which interacts with said holding device in order to assist in maintaining secure connection between said impaction device and said holding device.

9. A system as claimed in claim 8, wherein the distal region of said impaction device comprises a pin, said pin being operable to releasably seal said cavity, and wherein said pin interacts with said locking mechanism in order to allow or prevent the locking mechanism to interact with said holding device to effect locking and unlocking, respectively, of the impaction device to the holding device.

10. A system as claimed in claim 1, wherein an arrangement of said medical instrument and/or insert, said holding device, and said impaction device forms:
a means to create a low pressure or suction within the cavity; and
a means to maintain said low pressure or suction.

11. A system as claimed in claim 1, wherein the impaction device comprises a flange in the distal region, said flange being able to interact with the holding device to stabilise a siting of the impaction device on or in the holding device.

12. A system as claimed in claim 1, wherein the impaction device further comprises a mechanism to create a low pressure or suction within the cavity, said mechanism comprising a plunger in communication with said channel, said plunger being adjustable to draw or push the fluid within the channel and hence in said cavity.

13. A system as claimed in claim 1, wherein said system further comprises the fluid, said fluid being introduced to said system such that said fluid is present in said sealed cavity, wherein said fluid is liquid and there is substantially no gas present in said sealed cavity.

14. A system as claimed in claim 1, said system further comprising means to release fluid low pressure or suction.

15. A system as claimed in claim 1, said system further comprising:
means to introduce fluid to said cavity; and
means to expel surplus gas and/or liquid.

16. A system as claimed in claim 1, said system further comprising:
means to reduce cavity volume from an initial volume, said initial volume being a volume of said cavity when the holding device is inserted into said medical instrument to a predetermined position;
means to maintain said reduced cavity volume.

17. A system as claimed in claim 1, wherein said cover assembly further comprises:
at least one resilient and elastically deformable region associated with the cover assembly such that when elastically deformed in a stressed state there is natural bias of the resilient and elastically deformable region to revert to its unstressed state.

18. A system as claimed in claim 17, wherein the resilient and elastically deformable region is, or is associated with, a portion of the proximal surface of the cover assembly or a portion of the distal surface of the cover assembly.

19. A system as claimed in claim 1, wherein said cover assembly comprises a hole extending from and through the proximal surface to and through the distal surface.

20. A system as claimed in claim 1, wherein said cover assembly further comprises a hole in the distal surface beyond the seal, said hole extending into the cover assembly but not penetrating through the proximal surface.

* * * * *